United States Patent
Ptacek et al.

(10) Patent No.: US 7,306,911 B2
(45) Date of Patent: Dec. 11, 2007

(54) METHODS FOR ASSESSING RISK FOR CARDIAC DYSRYTHMIA IN A HUMAN SUBJECT

(75) Inventors: Louis Ptacek, Salt Lake City, UT (US); Ying-Hui Fu, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 234 days.

(21) Appl. No.: 10/475,452

(22) PCT Filed: Apr. 22, 2002

(86) PCT No.: PCT/US02/12652

§ 371 (c)(1),
(2), (4) Date: Oct. 21, 2003

(87) PCT Pub. No.: WO02/086447

PCT Pub. Date: Oct. 31, 2003

(65) Prior Publication Data

US 2005/0175995 A1    Aug. 11, 2005

Related U.S. Application Data

(60) Provisional application No. 60/286,146, filed on Apr. 24, 2001.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................... 435/6; 435/91.2; 536/23.1; 536/23.5; 536/24.31; 536/24.33

(58) Field of Classification Search .................... None
See application file for complete search history.

(56) References Cited

U.S. PATENT DOCUMENTS 6,274,332 B1 *   8/2001   Keating et al. .............. 435/7.2

OTHER PUBLICATIONS

Ptacek et al. American Journal of Human Genetics. Oct. 2001. 69: p. 230, Abstract #275.*

NCBI printout of SNPs in the KCNJ2 gene. National Center for Biotechnology, National Library of Medicine, NIH (Bethesda, MD, USA), 2006.*
Davies et al. Neurology. 2005. 65: 1083-1089.*
Plaster et al. May 2001. Cell. 105: 511-519.*
Bendahhou, Said, et al., "Defective Potassium Channel Kir2.1 Trafficking Underlies Andersen-Tawil Syndrome," The Journal of Biological Chemistry, vol. 278, No. 51, Dec. 19, 2003, pp. 51779-51785.
Donaldson, M.R., et al., "$PIP_2$ Binding Residues of Kir2.1 are Common Targets of Mutations causing Andersen Syndrome," Neurology 60, Jun. 2003, pp. 1811-1816.
Tristani-Firouzi, Martin, et al., Functional and Clinical Characterization of KCNJ2 Mutations Associated with LQT7 (Andersen Syndrome), The Journal of Clinical Investigation, Aug. 2002, vol. 110, No. 3, pp. 381-388.
Kubo, et al., "A Mutation of the Cloned Inward Rectifier K+ Channel, IRK1, which causes a Slowdown of the Activation and a Negative Shift of the Conductance Curve," Japanese Journal of Physiology. 1995, vol. 45, Supplement 1, p. S118, abstract 325.
Mylona, et al., "Detection of a High-Frequency Silent Polymorphin (C to T) in the Kir2.1 (KCNJ2) inwardly Rectifying Potassium Channel Gene by Polymerase Chain Reaction and Single Strand Conformation Polymorphism." Molecular and Cellular Probes, 1998, vol. 12, pp. 331-333, especially p. 332.
Splawski, et al., "Mutations in KCNJ2, an inward Rectifier Potassium Channel Gene, cause Andersen's Syndrome." American Journal of Human Genetics. Oct. 2001, vol. 69, Supplement 2, p. 230, abstract 276.

* cited by examiner

*Primary Examiner*—Carla Myers
(74) *Attorney, Agent, or Firm*—Jennifer M. McCallum, Esq.; The McCallum Law Firm, PC

(57) ABSTRACT

The present invention relates to methods for assessing the risk of a patient for developing a potentially fatal cardiac dysrhythmia and for diagnosing Andersen's Syndrome. A tissue sample from a patient is obtained and the DNA or proteins of the sample isolated. From the DNA and protein isolates the sequence of the KCNJ2 gene or the Kir2.1 polypeptide can be obtained. The KCNJ2 gene or the Kir2.1 can be screened for alteration as compared to the wile-type sequence. An alteration in a copy of the KCNJ2 gene or a Kir2.1 polypeptide indicates that the patient has a high risk for developing a cardiac dysrhythmia and can be diagnosed with Andersen's Syndrome. The invention also related to isolated nucleic acid molecules with one or more alterations as compared to the wild-type sequence.

5 Claims, 7 Drawing Sheets

SEQUENCE LISTING

```
<160> NUMBER OF SEQ ID NOS: 25

<210> SEQ ID NO 1
<211> LENGTH: 5243
<212> TYPE: DNA
<213> ORGANISM: Homo sapiens

<400> SEQUENCE: 1
cttttcttgc aggacatgtt ctctggatgt cagctgagtc attaaagtaa ctctgcatgt      60
cagtagacag accttggtag aaccacaagg ctcccagaga cacccatctc tcctcattt     120 tttggtgtgt gtgtcttcac cgaacattca aaactgtttc tccaaagcgt tttgcaaaaa     180
ctcagactgt tttccaaagc agaagcactg gagtccccag cagaagcgat gggcagtgtg     240
cgaaccaacc gctacagcat cgtctcttca gaagaagacg gtatgaagtt ggccaccatg     300
gcagttgcaa atggctttgg gaacgggaag agtaaagtcc acacccgaca acagtgcagg     360
agccgctttg tgaagaaaga tggccactgt aatgttcagt tcatcaatgt gggtgagaag     420
gggcaacggt acctcgcaga catcttcacc acgtgtgtgg acattcgctg gcggtggatg     480
ctggttatct tctgcctggc tttcgtcctg tcatggctgt tttttggctg tgtgttttgg     540
ttgatagctc tgctccatgg ggacctggat gcatccaaag agggcaaagc ttgtgtgtcc     600
gaggtcaaca gcttcacggc tgccttcctc ttctccattg agacccagac aaccataggc     660
tatggtttca gatgtgtcac ggatgaatgc ccaattgctg ttttcatggt ggtgttccag     720
tcaatcgtgg gctgcatcat cgatgctttc atcattggcg cagtcatggc caagatggca     780
aagccaaaga agagaaacga gactcttgtc ttcagtcaca atgccgtgat tgccatgaga     840
gacggcaagc tgtgtttgat gtggcgagtg ggcaatcttc ggaaaagcca cttggtgaa     900 gctcatgttc gagcacagct cctcaaatcc agaattactt ctgaagggga gtatatccct     960
ctggatcaaa tagacatcaa tgtttgggtt gacagtggaa tcgatcgtat atttctggtg    1020
tccccaatca ctatagtcca tgaaatagat gaagacagtc ctttatatga tttgagtaaa    1080
```

```
caggacattg acaacgcaga ctttgaaatc gtggtcatac tggaaggcat ggtggaagcc    1140
actgccatga cgacacagtg ccgtagctct tatctagcaa atgaaatcct gtggggccac    1200
cgctatgagc ctgtgctctt tgaagagaag cactactaca agtggactat tccaggttc     1260 cacaaaactt acgaagtccc caacactccc ctttgtagtg ccagagactt agcagaaaag    1320
aaatatatcc tctcaaatgc aaattcattt tgctatgaaa atgaagttgc cctcacaagc    1380
aaagaggaag acgacagtga aatggagtt ccagaaagca ctagtacgga cacgccccct    1440
gacatagacc ttcacaacca ggcaagtgta cctctagagc ccaggcccct acggcgagag    1500
tcggagatat gactgactga ttccttctct ggaatagtta ctttacaaca cggtctgttg    1560
gtcagaggcc aaaacagtt atacagatga cggtactggt caagatgggt caagcaagcg     1620
gccacaaggg actgaggcaa gcacaatggt ttcaaagaaa gactgtaagc tccatgatta    1680
gcataaagca ctaaccatgt ctccatgtga cccgatggca catagatgtt gtagaataag    1740
ttatgggttt ttatgttttg ttttgtgttt ttccaaaact tgaacttgca ggcaagcctt    1800
ggttgggtat ttgatttatc cagaatgctt ctctttaggg aacaaggatg tttttaatgg    1860
cataacaaag gcaagactct gccttaattt ttgaaaagct gctaactaca tgaacacaaa    1920
tgtgtatttt tgttgcagtg tagttttcct tttgtgtaat tttaaagtca gtgttgaatt    1980
ttattgaaag ctcatgatgc gcttcaaagt ggcaagtatt tggctattaa ctgccaaaac    2040
aagagcctga ttttttgagg ccagtaattc gtttgctaga attgattttt tttctctctc    2100
tctttgttac ataagggcat tatgtaacac tagccgaatg gtagcctctg ggttgttgtt    2160
tttttctttt cctccatgat gttaatgggt tatctcaaat tttaagttaa actacctaaa    2220
ataaatacca aagataatgc atattttgtc acagtggagc ttacacttaa agaaaacaa    2280 agccccatgg gctgccttga aatcaagaga caataacttt gaacctcagc aagaccttga    2340
accgccggtt catttttgcac cttattcaga aaatagagca tcatactcac cgagtctagt    2400
cagtgtagtg cttttaaaaa ttttgtcctt tcatgtaact tttttatttt aagaggaaga    2460
agaagaaagg ggcacacaca cacaataccg acgtctatcc tttcctgcta ggcagtgctg    2520
gccaggctca tgtgtagtgt gcgagatggt gatgtactct tatattttc tgggcttttc     2580 cttttgcaca ttccaaaatt catttcataa gacaagatct tcataggacc tccttggcat    2640
cctggcattc tcaaaactga gccatccagc atgaaagata aatgggttta aacccttgct    2700
gctgaattta ttgcctggac tgtcaggaca tcaccagccc accttcacct tagggaagat    2760
gccacacctg gcctccacac ttgctcttct gatcagtctg tctggattga gtcctacagt    2820
gtcagatagg gcggcaaatg ccaaagcagg gaaacaggga ggtgtggaca agccagtttg    2880
atgcagcact tcagatcaag tgcttaggaa ggagaggaaa cttgccttt ttatggcaga     2940 ggatagtaat gaaaatgtct cagtatttta gggtcaatga gagccataaa aatataacat    3000
aatcacaagt aaaggagata atggtctaaa acagctattt cccttttctg tgtgcatact    3060
tatgactgaa tgtgagctaa gcattttctc ctgtggagcc ctagagcagg ttactaagga    3120
aggacacatt gttttccaga agcctcccct gcctggctga ctgccttgct agaaacataa    3180
tttttttttt ctcactgaag ctcaataatg gaactctttt ttttttttt tttaatttaa    3240 agttccctat ttgtgaattc tgggattact gactttttctt tttaattgga gtctcaaaat    3300
caactctctt atggtattat atctctgtat gccattaaaa aacagcttgt tctagaatca    3360 tgtatttgt aaactgatgt ttgtgatggt ctctggttct tgaacagcca tatctgaatg    3420
ccgtgcctgc aaaactatga caatttttgc tgttttcagc cttcagattt gatggcttgg    3480
```

-continued

```
gaaactgagg tgttattttc aatgaaacaa agaaagagat gttaagcaag tggttgtttt    3540
agatccaaat gtaaaggcag gtttgggaag gtgtttaaag agttggagga attggggatt    3600
gagttgtaaa gaaaacttac agaagaggca acaatttggt tcttgacagt gagaggatat    3660
tgagggcttc agctgctgct attatgatgt tttgcaagg  aaaataatca aaccaaagag    3720
tattcagtga tatgtaaatt aaatgaagat acagtggaga atgggggtga ccacaaaaga    3780
ggctccccct aaacacacag tgctgccact taaaaagact tgagaaattt gaaggggggt    3840
gggtatgggg gggcaagaa  agagggaggg aaatctttca acttatttct gaaaagaga     3900 aaaaaatata aaatttctgg tgcacaggtt tgttttttca agaaaatttt gcagaagcta    3960 tgttttttaaa gtgtacattt tataaagttt atcagatatt ttcatattta aagccaaatg   4020
taaatagagg tctgtaaaga aaaataattg ccatagaaag tataatttca gtgcagtaat    4080
ttctgagagc tagtacctat atgctaccgg ttagcatggt tttagcaaat atataccagc    4140
cttataaggt tcgtattgct atgttcttct gttattatt  tcagcatgga ctgttcattt    4200
gaaacctttt tctagttatt agcgttttaa cagttacaag ctttaaatgg caatttttt     4260 tttttttttt tttttttttt tttttttgtc aagagccaag acacaggtaa tgcacgacat    4320
tgattgctgc attttacctt caaaatattt gtccttattg actgggtctc cttaattaat    4380
gtacacatgt cattagaatg cagacggagg ggactcacca tgaatatctg gggttgattc    4440
ccagatgtgt gttgcttctc tattgcaagc agattccctg ttggatttac ttcggattta    4500
ttccctttta aagaatttt  gcccatatct ggaagggcac tatattttg  ggaggagcca    4560 tagattcctg gttatcctat ttttaaacaa aatgtagaca aagtgaactc tattttgatt    4620
attgagaaag gagtagtttt ctatccctct aagagtatac ttgaatcaga cattttaagg    4680
atgtcactat ggcactgttg tcatttccaa attcctagaa aagtttgttt tactttgttt    4740
ttattctgtt aatgcattct ttcttctctt tacttccttt cttaccagta cactcctatc    4800
tcaactctgt ttatttgatg agttctgtcc cgtaaatcat atttccctta caattaataa    4860
atgtcacttc atattttata ataaaccact cagtaaaagc aaaagcttgt cctgagaagt    4920
agagtgagtt ctttttcact ctgtgtctaa taatgttaag gtgggaaaaa aaaagtgtg    4980 gcatagctac ctgcccatcc ccaaccctca gcaaagtaga atctcttttc tggtaatttt    5040
gggtttccgc tctgggctct ggcaagttga acaatcctag ccattgacaa tcgtgatagt    5100 tattatttt  ccatttgctg tcttttttgta tctaaagtct tcctattgta ctgcacaaac    5160
catggattgt acatattttt atatattatg tcttatttta ttatttctaa ataaaaaat     5220 taaaaattga aaacaaattc ttg                                            5243
```

<210> SEQ ID NO 2
<211> LENGTH: 427
<212> TYPE: PRT
<213> ORGANISM: Homo sapiens

<400> SEQUENCE: 2

Met Gly Ser Val Arg Thr Asn Arg Tyr Ser Ile Val Ser Ser Glu Glu
1               5                   10                  15

Asp Gly Met Lys Leu Ala Thr Met Ala Val Ala Asn Gly Phe Gly Asn
            20                  25                  30

Gly Lys Ser Lys Val His Thr Arg Gln Gln Cys Arg Ser Arg Phe Val
        35                  40                  45

Lys Lys Asp Gly His Cys Asn Val Gln Phe Ile Asn Val Gly Glu Lys

```
                    50                  55                  60
Gly Gln Arg Tyr Leu Ala Asp Ile Phe Thr Thr Cys Val Asp Ile Arg
 65                      70                  75                  80

Trp Arg Trp Met Leu Val Ile Phe Cys Leu Ala Phe Val Leu Ser Trp
                     85                  90                  95

Leu Phe Phe Gly Cys Val Phe Trp Leu Ile Ala Leu Leu His Gly Asp
                100                 105                 110

Leu Asp Ala Ser Lys Glu Gly Lys Ala Cys Val Ser Glu Val Asn Ser
                115                 120                 125

Phe Thr Ala Ala Phe Leu Phe Ser Ile Glu Thr Gln Thr Thr Ile Gly
                130                 135                 140

Tyr Gly Phe Arg Cys Val Thr Asp Glu Cys Pro Ile Ala Val Phe Met
145                 150                 155                 160

Val Val Phe Gln Ser Ile Val Gly Cys Ile Ile Asp Ala Phe Ile Ile
                165                 170                 175

Gly Ala Val Met Ala Lys Met Ala Lys Pro Lys Lys Arg Asn Glu Thr
                180                 185                 190

Leu Val Phe Ser His Asn Ala Val Ile Ala Met Arg Asp Gly Lys Leu
                195                 200                 205

Cys Leu Met Trp Arg Val Gly Asn Leu Arg Lys Ser His Leu Val Glu
210                 215                 220

Ala His Val Arg Ala Gln Leu Leu Lys Ser Arg Ile Thr Ser Glu Gly
225                 230                 235                 240

Glu Tyr Ile Pro Leu Asp Gln Ile Asp Ile Asn Val Gly Phe Asp Ser
                245                 250                 255

Gly Ile Asp Arg Ile Phe Leu Val Ser Pro Ile Thr Ile Val His Glu
                260                 265                 270

Ile Asp Glu Asp Ser Pro Leu Tyr Asp Leu Ser Lys Gln Asp Ile Asp
                275                 280                 285

Asn Ala Asp Phe Glu Ile Val Val Ile Leu Glu Gly Met Val Glu Ala
                290                 295                 300

Thr Ala Met Thr Thr Gln Cys Arg Ser Ser Tyr Leu Ala Asn Glu Ile
305                 310                 315                 320

Leu Trp Gly His Arg Tyr Glu Pro Val Leu Phe Glu Glu Lys His Tyr
                325                 330                 335

Tyr Lys Val Asp Tyr Ser Arg Phe His Lys Thr Tyr Glu Val Pro Asn
                340                 345                 350

Thr Pro Leu Cys Ser Ala Arg Asp Leu Ala Glu Lys Lys Tyr Ile Leu
                355                 360                 365

Ser Asn Ala Asn Ser Phe Cys Tyr Glu Asn Glu Val Ala Leu Thr Ser
                370                 375                 380

Lys Glu Glu Asp Asp Ser Glu Asn Gly Val Pro Glu Ser Thr Ser Thr
385                 390                 395                 400

Asp Thr Pro Pro Asp Ile Asp Leu His Asn Gln Ala Ser Val Pro Leu
                    405                 410                 415

Glu Pro Arg Pro Leu Arg Arg Glu Ser Glu Ile
                420                 425
```

<210> SEQ ID NO 3
<211> LENGTH: 20
<212> TYPE: DNA
<213> ORGANISM: Artificial Sequence Sequence
<220> FEATURE:
<223> OTHER INFORMATION: synthetic oligonucleotide

```
<400> SEQUENCE: 3
ccaaagcaga agcactggag                                                        20

<210> SEQ ID NO 4
<211> LENGTH: 21
<212> TYPE: DNA
<213> ORGANISM: Artificial Sequence Sequence
<220> FEATURE:
<223> OTHER INFORMATION: synthetic oligonucleotide

<400> SEQUENCE: 4
aatcaaatac ccaaccaagg c                                                      21

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5
gtgtttgatg tggcgagtgg                                                        20

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
attccactgt caaacccaac                                                        20

<210> SEQ ID NO 7
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 7
ggcaacggta cctcgcaga                                                         19

<210> SEQ ID NO 8
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 8
gggaacgata cctcgcagt                                                         19

<210> SEQ ID NO 9
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 9
caaccaaaac acacagccaa a                                                      21

<210> SEQ ID NO 10
<211> LENGTH: 19
```

```
<212> TYPE: DNA
<213> ORGANISM: Artificial Sequence
<220> FEATURE:
<223> OTHER INFORMATION: synthetic oligonucleotide

<400> SEQUENCE: 10
cggctgcctt cctcttctc                                                   19

<210> SEQ ID NO 11
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 11
cgggtgcctt cctcctctt                                                   19

<210> SEQ ID NO 12
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 12
cgggtgcctt cctcctctt                                                   19

<210> SEQ ID NO 13
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 13
gcttcacggc tgccttcc                                                    18

<210> SEQ ID NO 14
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 14
gtttctcttc tttggctttg c                                                21

<210> SEQ ID NO 15
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 15
ggcgagtggg caatcttcg                                                   19

<210> SEQ ID NO 16
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 16
```

-continued ggcgagtagg cagtcttca                                                    19

<210> SEQ ID NO 17
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 17
ctcaaatcat ataaggact gtc                                                23

<210> SEQ ID NO 18
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 18
ggcgagtggg caatcttcg                                                    19

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19
gtcgcgagta ggcaatgttt                                                   20

<210> SEQ ID NO 20
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 20
ctcaaatcat ataaggact gtc                                                23

<210> SEQ ID NO 21
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 21
aggacattga caacgcagac                                                   20

<210> SEQ ID NO 22
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 22
catggcagtg gcttccacc                                                    19

<210> SEQ ID NO 23
<211> LENGTH: 20
<212> TYPE: DNA
<213> ORGANISM: Artificial Sequence

```
-continued

<220> FEATURE:
<223> OTHER INFORMATION: synthetic oligonucleotide

<400> SEQUENCE: 23
catactggaa ggcatggtgg                                                    20

<210> SEQ ID NO 24
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 24
catgctggaa ggaatggtga                                                    20

<210> SEQ ID NO 25
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 25
gttttgtgga acctggaata g                                                  21
```

METHODS FOR ASSESSING RISK FOR CARDIAC DYSRYTHMIA IN A HUMAN SUBJECT

This application is a National Stage of International Application PCT/US02/12652, filed Apr. 22, 2002, which claims the benefit of U.S. Provisional Application 60/286,146, filed Apr. 24, 2001.

BACKGROUND OF THE INVENTION

1. The Field of the Invention

The present invention relates to methods of detecting risk for cardiac disease. More specifically, the present invention relates to genetic based methods for detecting a risk for a cardiac dysrhythmia in a patient and for diagnosing Andersen's Syndrome.

2. The Relevant Technology

Andersen's Syndrome (AS) is a rare disorder characterized by periodic paralysis, cardiac arrhythmias, and dysmorphic features. Canun, S., et al. (1999) *Am J Med Genet* 85: 147-56; Sansone, V. et al. (1997) *Ann Neurol* 42: 305-12; Tawil, R. et al. (1994) *Ann Neurol* 35: 326-30. The dysmorphology includes short stature, scoliosis, clinodactyly, wide-set eyes, small or prominent ears that are low set or slanted, a small chin, cleft pallet, and broad forehead. AS occurs either sporadically or as an autosomal dominant trait. In AS families, expression of the characteristic traits is highly variable. Thus, it is likely that the AS protein plays a complex role in development and cell excitability with some redundancy with other proteins.

The periodic paralyses and nondystrophic myotonias are a group of muscle disorders manifest by abnormal muscle relaxation (myotonia). This myotonia results from muscle hyperexcitability that sometimes transitions to inexcitability resulting in episodic weakness. Ventacular tachydysrhythmias are analogous to myotonia of skeletal muscle in that hyperexcitability leads to an abnormal, albeit highly organized, series of heart contractions that can also transition to inexcitability thus leading to death from cardiac dysrhythmias. The electrophysiological features of such diseases suggest an underlying defect in membrane excitability. Approximately 300,000 Americans die of cardiac dysrhythmias each year. Kannel, W. B. et al. (1987) *Am Heart J* 113, 799-804; Willich, S. N. et al. (1987) *Am J Cardiol* 60: 801-6.

Many of the persons who die of cardiac dysrhythmias do not exhibit heart problems prior to death. The fatal cardiac dysrhythmia may be triggered by aerobic exercise such as running. Thus, a patient may be at risk for cardiac dysrhythmias without exhibiting risk factors and without knowing to avoid certain types of activities or exercise. Moreover, certain medications are known to induce cardiac dysrhythmias in patients with heart conditions. However, when a patient does not exhibit any of the factors which would indicate a risk for cardiac dysrhythmias prior to a deadly episode, medical professionals cannot know what drugs to avoid prescribing to a patient.

Sudden Infant Death Syndrome (SIDS) is the leading cause of death in infants between 1 month and 1 year of age. Most SIDS deaths occur when a baby is between 1 and 4 months of age. SIDS is the medical term used to describe the sudden death of an infant under one year of age that remains unexplained after a complete investigation, which includes an autopsy, examination of the death scene, and review of the symptoms or illnesses the infant had prior to dying and any other pertinent medical history. A precise cause of SIDS is not known. However, sleep-induced arrhythmias may be a factor in SIDS. It has been hypothesized that changes in the activity of the autonomic nervous system during sleep could precipitate an arrhythmia resulting in sudden death.

The electrical properties of excitable tissues such as skeletal muscle, heart and neurons are determined, in part, by a number of ion channels that work in concert to provide properties appropriate for the function of each tissue. The first ion channel mutations which were shown to contribute to an episodic disorder were characterized about decade ago when mutations in SCN4A, which encodes a voltage-gated sodium channel, were shown to cause hyperkalemic periodic paralysis. Ptacek, L. J. et al. (1991) *Cell* 67: 1021-7; Rojas, C. V. et al. (1991) *Nature* 354: 387-9. This rare muscle disease formed the basis of the growing group now known as the channelopathies and led to predictions that cardiac dysrhythmias and epilepsies would be caused by mutations in homologous genes. Ptacek, L. J. et al. (1991) *Cell* 67: 1021-7. Similarities between these different episodic disorders suggested similar molecular bases of these disorders. The occurrence of both periodic paralysis and long QT (LQT) in Andersen's Syndrome strongly supports this hypothesis. Tawil, R. et al. (1994) *Ann Neurol* 35: 326-30. Since this initial discovery, periodic paralysis has been associated with mutations in voltage-gated $K^+$, $Na^+$, $Ca^{2+}$, and $Cl^-$ channels, while LQT has been associated with mutations in voltage-gated $K^+$ and $Na^+$ channels. Jen, J. & Ptacek, L. J., METABOLIC AND MOLECULAR BASES OF INHERITED DISEASE, pp. 5223-5238(C. R. Scriver et al., McGraw-Hill, 2001); Sanguinetti, M. (2001) *Cell* 104:569-580. To date, no human disorders involving cardiac and skeletal muscle have been attributed to mutations in inward rectifying $K^+$ channels.

Inward rectifier $K^+$ channels (Kir) play a role in controlling cell excitability and resting membrane potential in many different tissues including heart, brain, and skeletal muscle. Doupnik, C. A. et al. (1995) *Curr Opin Neurobiol* 5: 268-77; Jan, L. Y., & Jan, Y. N. (1997) *J Physiol* 505:267-82; Nichols, C. G., & Lopatin, A. N. (1997) *Annu Rev Physiol* 59,171-91. Generally, Kir channels contribute to the final repolarization phase of cardiac action potentials by passing small amounts of $K^+$ out of the cell and bringing the membrane potential back to resting membrane potential ($E_m$). Structurally, Kir channels resemble voltage-gated $K^+$ channels; however, they are missing the four N-terminal transmembrane domains including the S4 voltage sensor. Kir channels consist of an intracellular N-terminal domain, two transmembrane segments M1 and M2) flanking a pore region, and an intracellular C-terminal segment; M1 and M2 correspond to S5 and S6 of voltage-gated channels. Kir subunits are believed to form either homo- or heterotetramers. Yang, J. et al. (1995) *Neuron* 15: 1441-7.

Kir2.1 (IRK1), encoded by the gene KCNJ2, is a member of the Kir2.x family of inward rectifying $K^+$ channels expressed predominantly in heart, brain, and skeletal muscle. Kubo, Y. et al. (1993) *Nature* 362,127-33 Raab-Graham, K. F. et al. (1994) *Neuroreport* 5, 2501-5. The function of Kir2.1 has been studied primarily in the heart. It is classified as a strong inward rectifier, that is, almost no current passes through these channels at potentials positive to −40 mV. Thus, strong inward rectification prevents excess loss of $K^+$ during the plateau phase of the cardiac action potential, but allows outward $K^+$ flux during terminal repolarization and diastolic phases of the action potential. Sanguinetti, M. C., & Tristani-Firouzi, M., CARDIAC ELECTROPHYSIOLOGY: FROM CELL TO BEDSIDE, pp. 79-86., (D. P. Zipes, & J. Jalife, eds., W. B. Saunders, 2000).

Much less is known about the role of Kir2.1 in other tissues such as the brain and skeletal muscle. It is likely that the role of Kir2.1 in skeletal muscle and neurons is similar to its role in the heart by controlling the resting membrane potential and the terminal repolarization phase of the action potential. Interestingly, there is some evidence suggesting that Kir2.1 has some functional significance outside of modulating the action potential of neurons and myocytes. Kir2.1 knockout mice have a complete cleft of the secondary palate and a slight narrowing of the maxilla. Zaritsky, J. J. et al. (2000) *Circ Res* 87: 160-6. In rat, Kir2.1 MRNA is present by embryonic day 12 in bone associated structure of the head, limb, and body. Karschin, C., & Karschin, A. (1997) *Mol Cell Neurosci* 10, 131-48. These findings provide some evidence for an underlying developmental function of Kir2.1.

Currently the genetic cause of Andersen's Syndrome is not known. Moreover, persons with Andersen's Syndrome have a high risk for cardiac dysrhythmias. Accordingly it would be an advancement in the art to provide a gene responsible for the Andersen's Syndrome phenotype. It would be a further advancement to provide a diagnostic test for Andersen's Syndrome. It would be a further advancement to provide a method for detecting a risk for cardiac dysrhythmias in a patient.

BRIEF SUMMARY OF THE INVENTION

The method of the present invention has been developed in response to the present state of the art, and in particular, in response to the problems and needs in the art that have not yet been fully solved by the current state of medicine and genomics.

The present invention relates to a method of determining whether a patient has a heightened risk for a cardiac dysrhythmia. The method employs a genetic screen to determine if the patient has an alteration in single copy of the KCNJ2 gene. If the patient has an alteration in a KCNJ2 gene, the patient may have a heightened risk for a cardiac dysrhythmia as compared to a person without an alteration in his or her copies of the KCNJ2 gene. An alteration in a copy of the KCNJ2 gene may be a missense mutation, a deletion, an in-frame deletion, an insertion, or other mutation.

The screening of the patient's genome for alterations in the KCNJ2 gene may be accomplished in a variety of ways. For example, a tissue sample may be obtained from the patient. One or both copies of the patient's KCNJ2 gene may be isolated from the tissue sample, and one or both copies of the patient's KCNJ2 gene may be sequenced. The sequence of the patient's KCNJ2 gene may then be compared to the sequence of a wild-type KCNJ2 gene. A difference in the patient's KCNJ2 gene sequence compared to the wild-type sequence indicates an alteration in the patient's KCNJ2 gene, and it may be determined that the patient has a heightened risk for a cardiac dysrhythmia.

Another way of detecting an alteration in the patient'sKCNJ2 gene may include comparing the patient's KCNJ2 sequence with the sequences of known mutations. For example, a copy of one or both of the patient's KCNJ2 genes may be obtained and sequenced. The sequence of the patient's KCNJ2 gene may then be compared to a library of sequences of KCNJ2 genes with known mutations. If the sequence of the patient's KCNJ2 is identical to one of the sequences with a known mutation, then it may be determined that the patient has an alteration in a copy of his or her KCNJ2 genes. Currently, fourteen mutations in KCNJ2 genes have been isolated and sequenced from individuals and kindreds diagnosed with Andersen's Syndrome.

A probe may also be used to determine whether a patient has an alteration in a copy of his or her KCNJ2 gene. Such probes may contain a DNA sequence complementary to a portion of a KCNJ2 gene with a known mutation. The ability of the of the probe to bind to a copy of the patient's KCNJ2 gene may be tested under high stringency conditions. If the probe can bind to the patient's KCNJ2 gene, then it may be determined that the patient has a significant risk for a cardiac dysrhythmia. Such probes may be constructed using the portion of a KCNJ2 gene containing an alteration.

KCNJ2 encodes the polypeptides of the inward rectifying ion channel Kir2.1. The phenotypic characteristic of a person with Andersen's Syndrome can be attributed to alterations in Kir2.1. Thus, an alteration in Kir2.1 may indicate an alteration in KCNJ2. Thus, the sequence of a patient's Kir2.1 polypeptide may be determined and compared to the wild type sequence. Any alterations in the Kir2.1 polypeptide indicate an alteration in a KCNJ2 gene.

The invention also relates to methods of genetically diagnosing Andersen's Syndrome in a patient. The method for diagnosing Andersen's Syndrome may use the same steps as determining whether a patient has a high risk for a cardiac dysrhythmia. An alteration in the KCNJ2 gene may provide for the positive diagnosis of Andersen's Syndrome in a patient. An alteration in a copy of the KCNJ2 gene may be a missense mutation, a deletion, an in-frame deletion, or an insertion.

As with the method of determining a patient's risk for cardiac dysrhythmias in the method of diagnosing Andersen's Syndrome, the screening of the patient's genome for alterations in the KCNJ2 gene may be accomplished in a variety of ways. For example, a tissue sample may be obtained from the patient and the KCNJ2 gene isolated. The sequence of the KCNJ2 genes may be compared to wild-type or mutant sequences to determine whether the patient's sequence contains an alteration. Also probes may be used to detect an alteration. Other detection methods may involve the analysis of the Kir2.1 peptides encoded by KCNJ2.

In another aspect of the invention, a method of assessing a risk for human subject for Sudden Infant Death Syndrome (SIDS) is presented. The method may be used to screen an infant for the presence of an alteration in a copy of the KCNJ2 gene. Alternatively, a parent, or sibling of the infant may be screened for an alteration in a copy of their KCNJ2 genes. If the infant, parent, or sibling is found to have an alteration the KCNJ2 gene, then the infant may be at higher risk for SIDS. Such altered KCNJ2 genes which may place an infant at risk for SIDS may have the sequence of SEQ ID NO 1 as altered by on or more mutations selected from the group consisting of A440T, G658A, A874C, C880T, G1127T, G1132A, C635T, G881A, G1135A, C785T, C452G, G439A, a 6 nucleotide deletion beginning with nucleotide 1167, and a 12 nucleotide deletion beginning with nucleotide 512.

The screening for an alteration in a copy of the KCNJ2 gene may be accomplished in any of a number of ways. Generally a tissue sample such as blood, hair, oral swab, and the like will be taken for the screen. The KCNJ2 gene may be sequence and the sequence compared to a wild-type sequence or a sequence with a known alteration. Alternatively, the ability of a DNA binding probe containing a known alteration to bind to the KCNJ2 gene from the subject may be used. Also the Kir2.1 polypeptide may be used to screen for an alteration in the KCNJ2 gene.

The present invention also relates to isolated and purified nucleic acids which code for Kir2.1 polypeptides with an alteration in the polypeptide sequence. Such nucleic acids may be KCNJ2 genes with an alteration such as an insertion, a deletion, a missense mutation. Some Kir2.1 polypeptides have been isolated, purified and sequenced. For example an altered Kir2.1 polypeptide may have the sequence of SEQ ID No. 2 as altered by one or more alterations selected from the group consisting of D71V, G144S, N216H, R218W, G300V, V302M, Δ314-315, 95-S136F, R218Q, E303K, P186L, T75R, and D71N. Nucleic acid molecules that encode for the altered Kir2.1 polypepetide may be altered KCNJ2 genes having a sequence of SEQ ID NO 1 as altered by one or more mutations selected from the group consisting of A440T, G658A, A874C, C880T, G1127T, G1132A, C635T, G881A, G1135A, C785T, C452G, G439A, a 6nucleotide deletion begining with nucleotide 1167, and a 12 bp deletion beginning with nucleotide 512. Such altered KCNJ2 genes may be inserted into a vector or a cell for use in studies of the function of the Kir2.1 ion channel and the like.

BRIEF DESCRIPTION OF THE DRAWINGS

A more particular description of the invention briefly described above will be rendered by reference to specific embodiments thereof which may be understood by reference to the appended figures. The figures relate to only typical embodiments of the invention and are not therefore to be considered to be limiting of its scope. The invention will be described and explained with additional specificity and detail through the use of the accompanying drawings in which:

In FIG. 2A the structure of voltage-gated $K^+$ channels is shown. The S4 voltage-sensing segment is denoted with "+'s". In FIG. 2B the structure of inward rectifying $K^+$ channels is shown. The locations of identified mutations are represented on the structure.

FIG. 6A depicts WT Kir2.1 current elicited by 200 ms step depolarizations from −150 to −10 mV, from a holding potential of −70 mV. FIG. 6B depicts currents induced by injection of oocytes with $H_2O$ alone, D71V Kir2.1 and co-injection of D71V and WT Kir2.1. Small endogenous currents were recorded following injection of $H_2O$ or D71V. Co-injection of D71V and WT Kir2.1 resulted in inwardly rectifying $K^+$ currents. Note the smaller scale axis, compared to A. FIG. 6C shows instantaneous current-voltage relationships for oocytes injected with WT (filled squares), D71V (open triangles) and co-injected WT and D71V (filled circles) Kir2.1. Data represent mean±SEM, n=8-10 oocytes each group.

FIG. 7A shows WT Kir2.1 current elicited by the voltage protocol as shown. FIG. 7B depicts currents induced by injection of oocytes with $H_2O$ alone, R218W Kir2.1 and co-injection of R218W and WT Kir2.1. Small endogenous currents were recorded following injection of $H_2O$ or R218W. Co-injection of R218W and WT Kir2.1 resulted in inwardly rectifying $K^+$ currents whose amplitude was larger than that induced by co-injected D71V and WT (see FIG. 6). FIG. 7C illustrates instantaneous current-voltage relationships for oocytes injected with WT (filled squares), ½ WT (down triangles), R218W (up triangles) and co-injected WT and R218W (filled circles) Kir2.1. Oocytes were injected with 23 ng total cRNA, with the exception of ½ WT which was injected with 11.5 ng WT cRNA. Currents induced by injection of 11.5 ng WT were approximately one-half that induced by 23 ng WT Kir2.1. Data represent mean±SEM, n=8-10 oocytes each group.

DETAILED DESCRIPTION OF THE INVENTION

Figure 1:
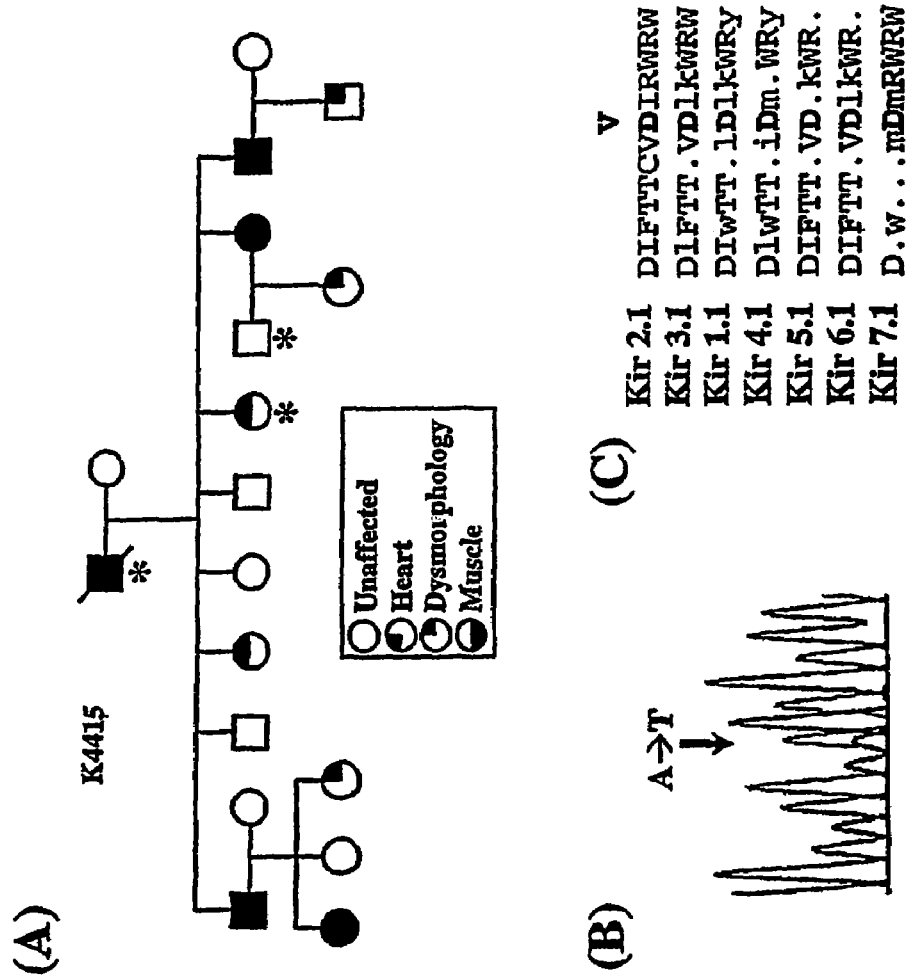
FIG. 1A is a graphic representation of the pedigree of kindred 4415 exhibiting variable expressivity and associated KCNJ2 mutation. Females are denoted with circles and males with squares. An "*" denotes an individual that was not included in the genome-wide linkage screen.
FIG. 1B is a graph illustrating a sequence chromatograph of an affected individual with an A to T transversion corresponding to the D71V mutation.
FIG. 1C depicts the amino acid alignment of one subunit from each of the seven members of the inward rectifying $K^+$ channels. The mutation is denoted above the alignment. Lowercase letters denote conservative amino acid changes, whereas a "." denotes anon-conservative amino acid change.

As discussed previously, Andersen's Syndrome is a rare disorder characterized by periodic paralysis, cardiac arrhythmias, and dysmorphic features. In the past Andersen's Syndrome has been diagnosed based on the phenotypic expression of the dysmorphic features, paralysis, and cardiac arrhythmias. AS occurs either sporadically or as an autosomal dominant trait. In AS families, expression of the characteristic traits is highly variable. Thus, AS may seemingly skip a generation because of the low level of phenotypic expression or non-penetrance in a person within the AS kindred. It is likely that the AS protein plays a complex role in development and cell excitability with some redundancy with other proteins.

The invention is based on the discovery that mutations in the Kir2.1 gene, KCNJ2, cause the triad of phenotypes in Andersen's Syndrome, including periodic paralysis, cardiac arrhythmias, and dysmorphic features. Andersen's Syndrome mutations involve residues in important functional domains. Several lines of evidence suggest that all of the identified mutations may result in functional consequences for Kir2.1. First, whence-expressed with wild-type subunits in *Xenopus* oocytes, D71V and R218W has dominant negative effects on Kir2.1 current. Second, fourteen mutations in KCNJ2 have been identified, and all of the identified mutations involve very highly conserved residues across all families of the Kir subunits. Third, two mutations were identified within the pore helix, which is a region conserved across voltage- and non-voltage-gated K$^+$ channels. Specifically, mutations in the GYG signature sequence of Kir channels lead to 1) a dominant negative effect and 2) a gain of function effect (Na$^+$ influx) in the weaver mouse. Tinker, A. et al. (1996) *Cell* 87: 857-68; Slesinger, P. A. et al. (1996) *Neuron* 16: 321-31. The weaver phenotype of ataxia, tremor, and hyperactivity is due to mutation of the second glycine to aserine in the signature sequence of the Kir subunit GIRK1. Finally, several mutations in Kir1.1 causing Bartter's syndrome, a renal disorder involving salt-wasting, hypokalemia, and metabolic acidosis, are in the same residue or similar functional domains as the mutations. Derst, C. et al. (1997) *Biochem Biophys Res Commun* 230: 641-5; Simon, D. B. et al. (1996) *Nat Genet* 14: 152-6. For instance, D74Y in Bartter's syndrome is in the equivalent residue of the D71V mutation. Bartter's mutation W99C and pore mutation V122E (position 150 in Kir2.1) reside in the same functional domain as the Δ95-98 and S136F mutations, respectively. A Bartter's mutation is also seen in the C-terminal tail of Kir1.1 at position 198 (Kir2.1 residue 248) similar to Andersen's R218W, R218Q, G300V, E303K, and Δ314-15.

Electrophysiological data show that WT current is significantly reduced when WT and mutant subunits are co-expressed at equal amounts. This suggests that onlyhomomultimers of WT subunits are functional. These data provide evidence against the possibility that the defect is due to aberrant channel co-assembly. If this were not the case, one would expect to see currents from co-injected oocytes at half the wild-type current. The strong dominant negative effects seen in voltage-clamp studies of co-injected subunits indicate that mutant subunits do co-assemble with wild-type subunits. Furthermore, the dominant negative effects documented are likely to result from either a disruption in channel trafficking or channel function once it is expressed in the plasma membrane; these studies cannot distinguish between these two possibilities. In the case that channels traffic correctly, K$^+$ current inhibition could be due to a number of causes, including physical obstruction of the intracellular vestibule or pore, altered affinity for K$^+$ ions, and increased affinity for Mg$^{2+}$ or polyamines that are known to block the pore.

The dominant negative effects on Kir2.1 function have consequences for cardiac and skeletal muscle excitability. LQT is a disorder of cardiac myocellular repolarization manifested by prolongation of the interval between the onset of ventricular depolarization (upstroke of the QRS complex) and termination of ventricular repolarization (end of the T wave). Dominantly inherited LQT is due to mutations in the cardiac Na$^+$ channel (SCN5A) or mutations in subunits encoding the cardiac delayed rectifier K$^+$ channels (HERG, KCNQ1, and KCNE1). Wang, Q. et al. (1995) *Cell* 80: 805-11; Curran, M. E. et al. (1995) *Cell* 80:795-803; Sanguinetti, M. C. et al. (1995) *Cell* 81:299-307; Splawski, I. et al. (1997) *Nat Genet* 17:338-40; Wang, Q. et al. (1996) *Nat Genet* 12:17-23. The commonpathophysiological feature of LQT isprolongationof the cardiac action potential due to either enhanced depolarizing current (Na channel mutations) orreduced repolarizing current (K$^+$ channel mutations). KCNJ2 is a novel LQT gene and is important in modulating cardiac excitability. Previously Kir2.1 was postulated to play an important, but not exclusive role, in generation of the cardiac inward rectifier current ($I_{K1}$). Nakalmura, T. Y. et al. (1998) *Am J Physiol* 274, H892-900; Wible, B. A. et al. (1995) *Circ Res* 76: 343-50. $I_{K1}$ contributes significant repolarizing current during the terminal phase of the cardiac action potential and serves as the primary conductance controlling the diastolic resting membrane potential ($E_m$) in a trial and ventricular myocytes. Sanguinetti, M. C., & Tristani-Firouzi, M., CARDIAC ELECTROPHYSIOLOGY: FROM CELL TO BEDSIDE, pp. 79-86., (D. P. Zipes, & J. Jalife, eds., W. B. Saunders, 2000). Dominant-negative mutations in Kir2.1 prolong cardiac action potentials in affected individuals by reducing the amount of repolarizing current during the terminal phase. Action potential prolongation creates the substrate for early after depolarizations (EADs), the presumptive trigger for ventricular tachycardia. Tristani-Firouzi, M. et al. (2001) *Am J Med* 110: 50-9. Whether mutations in Kir2.1 alter the diastolic $E_m$ in cardiomyocytes is not known.

Kir channels play an important, albeit secondary, role in controlling resting Em in skelet al muscle. Horowicz, P. & Spalding, B. C., MYOLOGY: BASIC AND CLINICAL, pp. 405-422 (A. G. Engel, and C. Franzini-Armstrong, eds., McGraw-Hill, Inc. 1994). While Kir2.1,2.2, and 2.4 are expressed in skelet al muscle, the relative contribution of each subfamily member is not known. Kubo, Y. et al. (1993) *Nature* 362, 127-33; Takahashi, N. et al. (1994) *J Biol Chem* 269: 23274-9; Topert, C. et al. (1998) *J Neurosci* 18:4096-105. These data identify the importance of Kir2.1 in modulating skelet al muscle excitability. The reduced resting K$^+$ conductance due to Kir2.1 mutations might allow the unopposed chloride conductance to shift $E_m$ in the depolarized direction, toward the equilibrium potential of chloride. Depolarizationof the cellmembranewould inactivate Na$^+$ channels, which would be unavailable for initiation and propagation of action potentials. Reduced Na$^+$ current is proposed to be a common feature in the pathophysiology of hypokalemic periodic paralysis (HypoKPP). Jurkat-Rott, K. et al. (2000) *Proc Natl Acad Sci USA* 97, 9549-54; Ruff, R. L. (2000) *Proc Natl Acad Sci USA* 97: 9832-3; Ruff, R. L., & Cannon, S. C. (2000) *Neurology* 54:2190-2. Individuals with HypoKPP caused by mutations in the L-type Ca$^{2+}$ channel, reduced availability of Na$^+$ channels is postulated to be linked to reduced activity of a member of the Kir super family, the $K_{ATP}$ channel. Ptacek, L. J. et al. (1994) *Cell* 77, 863-868; Fouad, G. et al. (1997) *Neuromuscular Disorders* 7: 33-38; Ruff, R. L. (1999) *Neurology* 53:1556-63; Tricarico, D. et al. (1999) *J Clin Invest* 103: 675-82. Thus, these data and that of others, support the importance of Kir channels in modulating skelet al muscle excitability. Ruff, R. L. (1999) *Neurology* 53:1556-63; Tricarico, D. et al. (1999) *J Clin Invest* 103: 675-82.

Kir2.1 has a significant role in development The importance of ion channels in the function of muscle, heart, and brain is indisputable as evidenced by the plethora of mutations found associated with just periodic paralysis, LQT, and epilepsy. However, an intriguing new niche for ion channels in development has just begun to be recognized, especially with the characterization of the weaver mouse. A mutation in the pore region of the G-protein coupled inward rectifier potassium channel GIRK2 was found to be associated with the defects in neural development of weaver. Patil, N. et al. (1995) *Nat Genet* 11, 126-9.

These findings in AS and Kir2.1 support this link between ion channels and developmental signaling. The role of K$^+$ channels in craniofacial development has not previously been reported. Andersen's Syndrome and the Kir2.1 knockout mouse both provide evidence that ion channels play a previously unrecognized role in this process. Developmental characteristics of the Kir2.1 mouse, including narrowing of the maxilla and complete cleft of the secondary palate, provide some intriguing links to the facial dysmorphology seen in many Andersen's patients. Zaritsky, J. J. et al. (2000) *Circ Res* 87: 160-6. A study on Kir2.1 MRNA expression in rat embryos at embryonic day 12 shows that Kir2.1 MRNA is associated with bone structures in the head, limbs and body. Karschin, C., & Karschin, A. (1997) *Mol Cell Neurosci* 10, 131-48. Whether or not Kir2.1 is expressed early enough for craniofacial and other bone morphogenetic events has not been investigated.

There is evidence suggesting that Kir2.1 might be expressed in neural crest cells, a population of cells that eventually differentiate into part of the peripheral nervous system, skin pigment cells, and into the craniofacial bones. In the promoter region of KCNJ2 there is a putative binding site for the transcription factor AP-2. Redell, J. B., & Tempel, B. L. (1998) *J Biol Chem* 273:22807-18. This transcription factor is expressed predominantly in neural crest cells. Schorle, H. et al. (1996) *Nature* 381: 235-8; Zhang,J. et al. (1996) *Nature* 381: 238-41. Investigation of Kir2.1 expression patterns prior to day 12 in mouse embryos could enhance the understanding of the putative role that Kir2.1 plays in craniofacial and skelet al morphogenesis. Recent in situ hybridization studies have shown that Kir2.1 is expressed in neural crest cells of chick embryos. (Data not shown).

Some evidence exists that alterations in KCNJ2 may be responsible inpart for conditions such as fetal wastage and sudden infant death sysndrome (SIDS). Andersen's Syndrome is an extremely rare disorder. Moreover, there is a high rate of sporadic mutations found in the disease; as many as one half of alterations may have resulted from a sporadic mutation. This evidence indicates that there is strong natural selection against the Andersen's Syndrome and mutations in KCNJ2. Because Kir2.1 affects the development of many organs and body systems, it may also play a role in fetal wastage. Additionally, because cardiac dysrhythmias have been implicated in SIDS, alterations in KCNJ2 and Kir2.1 may also predispose an infant to a risk for SIDS. Accordingly a screen for alterations in KCNJ2 and Kir2.1 as discussed below, may be used to assess the risk of SIDS or fetal wastage.

Based on the discovery that KCNJ2 gene is responsible for the Andersen's Syndrome phenotype including a risk for cardiac dysrhythmias, a genetic screen has been developed for determining if a patient has a heightened risk for a cardiac dysrhythmia. The present invention relates to a method of determining whether a patient has a heightened risk for a cardiac dysrhythmia. Because of the variable expression of the Andersen's Syndrome phenotype even within a kindred, the method may be used to diagnose persons who show little or no outward signs of Andersen's Syndrome, but who still have a high risk of the heart problems associated with AS. The genetic screen may be used to determine if the patient has an alteration in a single copy of the KCNJ2 gene. If the patient has an alteration in a KCNJ2 gene, the patient may have a heightened risk for a cardiac dysrhythmia as compared to a person without an alteration in his or her copies of the KCNJ2 gene. The alterations in the KCNJ2 gene include mutations and polymorphisms. Included among the mutations are frameshift, nonsense, splice, regulatory and missense mutations. Any method which is capable of detecting the mutations and polymorphisms described herein can be used. Such methods include, but are not limited to, DNA sequencing, allele-specific probing, mismatch detection, single stranded conformation polymorphism detection and allele-specific PCR amplification.

KCNJ2 mutations cause increased risk for cardiac dysrhythmia and are the genetic cause for Andersen's Syndrome. Many different mutations can occur in KCNJ2. In order to detect the presence of alterations in the KCNJ2 gene, a biological sample such as blood is prepared and analyzed for the presence or absence of a given alteration of KCNJ2. To detect the increased risk for cardiac dysrhythmia or for the lack of such increased risk, a biological sample is prepared and analyzed for the presence or absence of a mutant allele of KCNJ2. Results of these tests and interpretive information are returned to the health care provider for communication to the tested individual. Such diagnoses may be performed by diagnostic laboratories or, alternatively, diagnostic kits are manufactured and sold to health care providers or to private individuals for self-diagnosis.

The presence of a hereditary condition such as Andersen's Syndrome or an increased risk for cardiac dysrhythmias may be ascertained by testing any tissue of a human for mutations of the KCNJ2 gene. For example, a person who has inherited a germine KCNJ2 mutation may be prone to develop a fatal cardiac dysrhythmia. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells formulations of the KCNJ2 gene. Alteration of a wild-type KCNJ2, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. Another approach is the single-stranded conformation polymorphism assay (SSCP). Orita M, et al. (1989) *Proc. Natl. Acad. Sci. USA* 86:2766-2770. This method does not detect all sequence changes, especially if the DNA fragment size is greater than 200 bp, but can be optimized to detect most DNA sequence variations. The reduced detection sensitivity is a disadvantage, but the increased throughput possible with SSCP makes it an attractive, viable alternative to direct sequencing for mutation detection on a research basis. The fragments which have shifted mobility on SSCP gels are then sequenced to determine the exact nature of the DNA sequence variation. Other approaches based on the detection of mismatches between the two complementary DNA strands include clamped denaturing gel electrophoresis (CDGE) (Sheffield V C, et al. (1991) *Am. J Hum. Genet.* 49:699-706), heteroduplex analysis (HA) (White M B, et al. (1992) *Genomics* 12:301-306), and chemical mismatch cleavage (CMC) (Grompe M, et al., (1989) *Proc. Natl. Acad. Sci. USA* 86:5855-5892). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a review by Grompe (1993). Grompe M (1993) *Nature Genetics* 5:111-117. Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result. Elghanian R, et al. (1997) *Science* 277:1078-1081.

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of LQTS cases. Southern blots displaying hybridizing fragments (differing in length from control DNA when probed with sequences near or including the KCNJ2 locus) indicate a possible mutation. If restriction enzymes which produce very large restriction fragments are used, then pulsed field gel electrophoresis (PFGE) is employed.

Detection of point mutations may be accomplished by molecular cloning of the KCNJ2 allele and sequencing the allele using techniques well known in the art. Also, the gene or portions of the gene may be amplified, e.g., by PCR or other amplification technique, and the amplified gene or amplified portions of the gene may be sequenced.

There are six well known methods for a more complete, yet still indirect, test for confirming the presence of a susceptibility allele: 1) single stranded conformation analysis (SSCP) Orita M, et al. (1989) *Proc. Natl. Acad. Sci. USA* 86:2766-2770); 2) denaturing gradient gel electrophoresis (DGGE) (Wartell R M, et al. (1990) *Nucl. Acids Res.* 18:2699-2705; Sheffield V C, et al. (1989) *Proc. Natl. Acad. Sci. USA* 86:232-236); 3) RNase protection assays (Filklelstein et al., 1990; Kinszler K W, et al. (1991) *Science* 251:1366-1370.); 4) allele-specific oligonucleotides (ASOs) (Conner B J, et al. (1983) *Proc. Natl. Acad. Sci. USA* 80:278-282. ); 5) the use of proteins which recognize nucleotide mismatches, such as the *E. coli* mutS protein (Modrich P (1991) *Ann. Rev. Genet.* 25:229-253); and 6) allele-specific PCR (Ruano G & Kidd K K (1989) *Nucl. Acids Res.* 17:8392). For allele-specific PCR, primers are used which hybridize at their 3' ends to a particular KCNJ2 mutation. If the particular mutation is not present, an amplification product is not observed. Amplification Refractory Mutation System (ARMS) can also be used. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the mutation found in that individual. Other techniques for detecting insertions and deletions known in the art can be used.

In the first three methods (SSCP, DGGE and RNase protection assay), a new electrophoretic band appears. SSCP detects a band which migrates differentially because the sequence change causes a difference in single-strand, intramolecular base pairing. RNase protection involves cleavage of the mutant polynucleotide into two or more smaller fragments. DCGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe which is complementary to the human wild-type KCNJ2 gene coding sequence. The riboprobe and either mRNA or DNA isolated from the person are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the MRNA or DNA. The riboprobe need not be the full length of the mRNA or gene but can be a segment of either. If the riboprobe comprises only a segment of the mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton R G, et al. (1988) *Proc. Natl. Acad. Sci. USA* 85:4397-440; Shenk T E, et al. (1975) *Proc. Natl. Acad. Sci. USA* 72:989-993; Novack D F, et al. (1986) *Proc. Natl. Acad. Sci. USA* 83:586-590. Alternatively, mismatches can be detected by shifts in the electrophoretic mobility of mismatched duplexes relative to matched duplexes. See, e.g., Cariello N F (1988) *Am. J Human Genetics* 42:726-734. With either riboprobes or DNA probes, the cellular mRNA or DNA which might contain a mutation can be amplified using PCR (see below) before hybridization. Changes in DNA of the KCNJ2 gene can also be detected using Southern hybridization, especially if the changes are gross rearrangements, such as deletions and insertions.

DNA sequences of the KCNJ2 gene which have been amplified by use of PCR may also be screened using allele-specific probes. These probes are nucleic acid oligomers, each of which contains a region of the gene sequence harboring a known mutation. For example, one oligomer may be about 30 nucleotides in length, corresponding to a portion of the gene sequence. By use of a battery of such allele-specific probes, PCR amplification, products can be screened to identify the presence of a previously identified mutation in the gene. Hybridization of allele-specific probes with amplified KCNJ2 sequences can be performed, for example, on a nylon filter. Hybridization to a particular probe under high stringency hybridization conditions indicates the presence of the same mutation in the tissue as in the allele-specific probe.

Nucleic acid analysis via microchip technology is also applicable to the present invention. In this technique, thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia J G, et al. (1996) *Nature Genetics* 14:441-447; Shoemaker D D, et al. (1996) *Nature Genetics* 14:450-456; Chee M, et al. (1996) *Science* 274: 610-614; Lockhart D J, et al. (1996) *Nature Biotechnology* 14:1675-1680; DeRisi J, et al. (1996) *Nat. Genet.* 14:457-460; Lipshutz R J, et al. (1995) *Biotechniques* 19:442-447. This method has already been used to screen people for mutations in the breast cancer gene BRCA1. Hacia J G, et al. (1996) *Nature Genetics* 14:441-447.

The most definitive test formutations in a candidate locus is to directly compare genomic KCNJ2 sequences from patients with those from a control population. Alternatively, one could sequence messenger RNA after amplification, e.g., by PCR, thereby eliminating the necessity of determining the exon structure of the candidate gene.

Mutations from patients falling outside the coding region of KCNJ2 can be detected by examining the non-coding regions, such as introns and regulatory sequences near or within the genes. An early indication that mutations in noncoding regions are important may come from Northern blot experiments that reveal messenger RNA molecules of abnormal size or abundance in patients as compared to control individuals.

Alteration of KCNJ2 expression can be detected by any techniques known in the art. These include Northern blot analysis, PCR amplification and RNase protection. Diminished mRNA expression indicates an alteration of the wild-type gene. Alteration of wild-type (genes can also be detected by screening for alteration of wild-type Kir2.1 protein. For example, monoclonal antibodies immunoreactive with Kir2.1 can be used to screen a tissue. Lack of cognate antigen would indicate a mutation. Antibodies specific for products of mutant alleles could also be used to detect mutant gene product. Such immunological assays can be done in any convenient formats known in the art. These include Western blots, immunohistochemical assays and ELISA assays. Any means for detecting an altered Kir2.1 protein can be used to detect alteration of wild-type KCNJ2 genes. Functional assays, such as protein binding determinations, can be used. In addition, assays can be used which detect Kir2.1 biochemical function. Finding a mutant KCNJ2 gene product indicates alteration of a wild-type KCNJ2 gene.

Mutant KCNJ2 genes or gene products can also be detected in other human body samples, such as serum, stool, urine and sputum. The same techniques discussed above for detection of mutant genes or gene products in tissues can be applied to other body samples. By screening such body samples, a simple early diagnosis can be achieved for Andersen's Syndrome or a risk for cardiac dysrhythmia.

Initially, the screening method involves amplification of the relevant KCNJ2 sequence. Alternatively, the screening method involves anon-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences, the biological sample to be analyzed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of the genes. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety. A number of these variations are well known.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently lined to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$-$10^6$ increase in sensitivity. For example, the preparation of oligodeoxynucleotide-alkaline phosphatase conjugates and their use as hybridization probes are well known.

Two-step label amplification methodologies are known in the art. These assays work on the principle that a small ligand (such as digoxigenin, biotin, or the like) is attached to a nucleic acid probe capable of specifically binding the target gene. Allele specific probes are also contemplated within the scope of this example.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. In a second example, the small ligand is recognized by a second ligand-enzyme conjugate that is capable of specifically complexing to the first ligand. A well known embodiment of this example is the biotin-avidin type of interactions. Methods for labeling nucleic acid probes and their use in biotin-avidin based assays are well known.

It is also contemplated within the scope of this invention that the nucleic acid probe assays of this invention will employ a cocktail of nucleic acid probes capable of detecting the gene or genes. Thus, in one example to detect the presence of KCNJ2 in a cell sample, more than one probe complementary to KCNJ2 is employed and in particular the number of different probes is alternatively 2, 3, or 5 different nucleic acid probe sequences. In another example, to detect the presence of mutations in the KCNJ2 gene sequence in a patient, more than one probe complementary to KCNJ2 is employed where the cocktail includes probes capable of binding to the allele-specific mutations identified in populations of patients with alterations in KCNJ2. In this embodiment, any number of probes can be used.

Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The general methods of purification of nucleic acids are described, e.g., in Sambrook J, et al. (1989) Molecular Cloning: A Laboratory Manual, 2nd Ed. (Cold Spring Harbor Laboratory, Cold Spring Harbor, N.Y.) or Ausubel F M, et al. (1992) Current Protocols in Molecular Biology, (John Wiley and Sons, New York, N.Y.).

The polynucleotides of the present invention may also be produced by chemical synthesis, e.g., by the phosphoramidite method described by Beaucage and Caruthers or the triester method according to Matteucci and Caruthers and may be performed on commercial, automated oligonucleotide synthesizers. Matteucci M D & Caruthers M H (1981) *J Am. Chem. Soc.* 103:3185; Beaucage S L, & Caruthers M H (1981) Tetra. Letts. 22:1859-1862. A double-stranded fragment may be obtained from the single-stranded product of chemical synthesis either by synthesizing the complementary strand and annealing the strand together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Such vectors may be prepared by means of standard recombinant techniques well known in the art and discussed, for example, in Sambrook J, et al. (1989) Molecular Cloning: A Laboratory Manual, 2nd Ed. (Cold Spring Harbor Laboratory, Cold Spring Harbor, N.Y.) or Ausubel F M, et al. (1992) Current Protocols in Molecular Biology, (John Wiley and Sons, New York, N.Y.).

An appropriate promoter and other necessary vector sequences will be selected so as to be functional in the host, and may include, when appropriate, those naturally associated with the KCNJ2 or other gene. Examples of workable combinations of cell lines and expression vectors are described in Sambrook J, et al. (1989) *Molecular Cloning: A Laboratory Manual,* 2nd Ed. (Cold Spring Harbor Laboratory, Cold Spring Harbor, N.Y.) or Ausubel F M, et al. (1992) Current Protocols in Molecular Biology, (John Wiley and Sons, New York, N.Y.); see also, e.g., Metzger D, et al. (1988) *Nature* 334:31-36. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for met allothionein, 3-phosphoglycerate kinase or other glycolytic enzymes such as enolase or glyceraldehyde-3-phosphate dehydrogenase, enzymes responsible for maltose and galactose utilization, and others. Appropriate non-native mammalian promoters might include the early and late promoters from SV40 or promoters derived from murine Molony leukemia virus, mouse tumor virus, avian sarcoma viruses, adenovirs II, bovine papilloma virus orpolyoma. Insect promoters may be derived from baculovirus. Fiers W, et al. (1978) *Nature* 273:113-120. In addition, the construct may be joined to an amplifiable gene (e.g., DHFR) so that multiple copies of the gene may be made. For appropriate enhancer and other expression control sequences, see also Enhancers and Eukaryotic Gene Expression, Cold Spring Harbor Press, Cold Spring Harbor, N.Y. (1983).

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc., b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed invitro, and the resulting RNA introduced into the host cell by well-known methods, e.g., by injection (see, Kubo T, et al. (1988) *FEBS Lett.* 241:119), or the vectors can be introduced directly into host cells by methods well known in the art, which vary depending on the type of cellular host, including electroporation; transfection employing calcium chloride, rubidium chloride calcium phosphate, DEAE-dextran, or other substances; microprojectile bombardment; lipofection; infection (where the vector is an infectious agent, such as a retroviral genome); and other methods. See generally, Sambrook J, et al. (1989) *Molecular Cloning: A Laboratory Manual,* 2nd Ed. (Cold Spring Harbor Laboratory, Cold Spring Harbor, N.Y.) and Ausubel F M, et al. (1992) Current Protocols in Molecular Biology, (John Wiley and Sons, New York, N.Y.). The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the KCNJ2 nucleic acid or portions thereof in vectors or other expression vehicles incompatible prokaryotic or eukaryotic host cells. The most commonly used prokaryotic hosts are strains of *Escherichia coli,* although other prokaryotes, such as *Bacilluis subtilis* or Pseudonmonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby W B and Pastan I H (eds.) (1979) *Cell Culture. Methods in Enzymology volume* 58 (Academic Press, Inc., Harcourt Brace Jovanovich (New York)). Examples of commonly used mammalian host cell lines are VERO and HeLa cells, Chinese hamster ovary (CHO) cells, and W138, B, and COS cell lines, although it will be appreciated by the skilled practitioner that other cell lines may be appropriate, e.g., to provide higher expression, desirable glycosylation patterns, or other features. An example of a commonly used insect cell line is SF9.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of Kir2.1 or other polypeptides.

The mutated genes and their encoded proteins may be used in methods of diagnosing a patient with Andersen's Syndrome or to further study the properties of Kir2.1. KCNJ2 genes with an alteration such as a insertion, a deletion, a missense mutation are presented herein. Such altered KCNJ2 genes may have the sequence of SEQ ID NO 1 as altered by one or more mutations selected from the group consisting of A440T, G658A, A874C, C880T, G1127T, G1132A, C635T, G881A, G1135A, C785T, C452G, G439A, a 6 nucleotide deletion beginning with nucleotide 1167, and a 12 bp deletion beginning with nucleotide 512. Altered Kir2.1 polypeptides which are encoded by altered KCNJ2 genes have been isolated, purified and sequenced. For example, Kir2.1 proteins have been isolated which have alternations in highly conserved positions within the Kir2.1 protein. Examples of such proteins are proteins which have the amino acid sequence of SEQ ID NO 2 as altered by one or more of the following alterations: D71V, G144S, N216H, R218W, G300V, V302M, Δ314-315, Δ95-98, S136F, R218Q, E303K, P186T75R, and D71N.

In order to better describe the details of the present invention, the following discussion is divided into six sections: (1) patients with Andersen's Syndrome have variable expressivity; (2) an Andersen's Syndrome allele is located on chromosome 17q23; (3) KCNJ2, CACNG1 and SCN4A are candidate genes for Andersen's Syndrome; (4) D71V segregates with Andersen's Syndrome; (5) thirteen additional mutations have been identified in Andersen's Syndrome probands; and (6) D71V and R218W result in a dominant negative effect on Kir2.1 current in *Xenopus* oocytes.

Patients with Andersen's Syndrome Have Variable Expressivity

There are no published clinical criteria for the diagnosis of Andersen's Syndrome. The criteria based upon the clinical data gathered from the three largest published case series on Andersen's Syndrome, a set of criteria were developed. Canun, S., et al. (1999) *Am J Med Genet* 85: 147-56; Sansone, V. et al (1997) *Ann Neurol* 42: 305-12; Tawil, R. et al. (1994) *Ann Neurol* 35:326-30. These criteria take into account the clinical observation that Andersen's Syndrome shows variable penetrance.

Individuals were classified as affected if two of three of the following criteria were met: clearcut episodes of muscle wellness, cardiac involvement, and dysmorphology. Muscle weakness was based on one of the following criteria: 1) a typical history of weakness with rest following exertion or prolonged rest, 2) an a typical history but with a documented physical exam during an attack demonstrating hypo reflexia with preserved sensation, 3) an atypical history without a documented exam but with unexplained intraictal serum hypo/hyperkalemia, or 4) an atypical history without a documented exam or serum potassium levels but with an abnormal exercise nerve conduction study. McManis, P. G. et al. (1986) *Muscle Nerve* 9,704-10. Cardiac involvement was determined by the presence of prolonged QTc on twelve lead EKG according to standard criteria. Martin, A. B. et al. (1995) *Am J Cardiol* 75, 950-2 Schwartz, P. J. et al. (1993) *Circulation* 88: 782-4. Dysmorphology was noted if there was the presence of two or more of the following: 1) low set ears, 2) hypertelorism, 3) small mandible, 4) clinodactyly, or 5) syndactyly. At risk individuals expressing one of the three major phenotypes of Andersen's Syndrome were classified as "probably affected". Individuals were classified as unaffected if none of the criteria were fulfilled. One of the authors (R. T.), who was blinded to the results of the mutational analysis, reviewed the clinical information on each subject and confirmed their diagnostic classification.

A total of 32 unrelated Andersen's Syndrome kindreds were identified meeting the defined diagnostic criteria. Fourteen different mutations were found in the KCNJ2 gene of 22 out of the 32 kindreds. Most kindreds were small, consisting of one to three affected individuals. Affected individuals showed marked variability in the phenotypic expression of the disease. Whereas one individual, typically the index case, manifested the full Andersen's triad, other affected individuals demonstrated only one or two of the major characteristics of this disorder. Dysmorphic features ranged from negligible deformities of the digits to very prominent facial dysmorphisms. Cardiac involvement ranged from a symptomatic LQT and ventricular ectopy, to syncope from sustained ventricular tachycardia, to recurrent torsades depointes and cardiac arrest requiring treatment with an implantable defibrillator. Attacks of paralysis were associated with hypo-, hyper-, or normokalemia Although serum potassium levels during attacks differed among kindreds they were consistent within an individual kindred.

The expressivity of Andersen's Syndrome is variable. Andersen's Syndrome is incompletely penetrant and variably expressed. Severity ranges from non-penetrant (4 of 28 affected individuals), 1 of 3 characteristics (5 of 28), 2 of 3 characteristics (6 of 28), to s affected with 3 out of 3 characteristics (13 of 28). Several conditions could explain such pleiotropy. First, normal variation in mutant versus wild-type subunit expression levels could explain some of this variation. It was shown in electrophysiological studies with the weaver mutation that lower levels of mutant subunit in comparison to wild-type reduced channel function. However, when levels of mutant subunits were increased, these $K^+$-specific channels began to aberrantly pass $Na^+$ current. Slesinger, P. A. et al. (1996) *Neuron* 16: 321-31. In addition to mutant subunit expression levels, normal variations in expression of overlapping channels or in non-channel proteins within the same functional pathway as Kir2.1 could cause phenotypic variation. External environmental factors could also have some influence on the expression of the Andersen's phenotypes. Because of the variable expressivity, it is likely that some Andersen's patients are diagnosed as LQT or periodic paralysis patients instead.

An Andersen's Syndrome Allele Is Located on Chromosome 17q23

Figure 3:
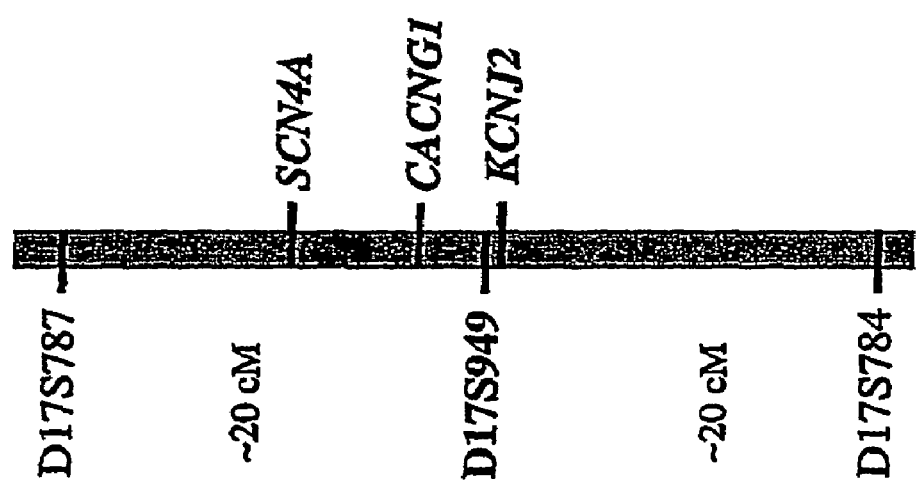
FIG. 3 depicts a map of the Andersen's Syndrome locus. Markers D17S787 and D17S784 are the proximal and distal recombinant boundaries respectively. Distance is marked between each recombinational boundaries and D17S949. The location of three candidates is shown to the right.

In order to identify the Andersen's locus, approximately 400 polymorphic markers were analyzed across the entire genome in 15 individuals of kindred 4415 (FIG. 1A). Kindred 4415 is well-established as an AS family, individuals were classified as affected in this analysis if they exhibited one of the three main characteristics of Andersen's Syndrome as described previously. One marker (D17S949) from the set of 400 maximized at θ=0 with a LOD score of 3.23. The simulated maximum LOD score for this kindred for a 5 allele system was 3.21 at θ=0. Marker D17S787 set the proximal recombinant boundary with a LOD score of –∞ at θ=0, whereas D17S784 set the distal recombinant boundary with a LOD score of–∞ at θ=0. This region corresponds to a genetic region of over 40 cM on chromosome 17q23 (FIG. 3).

An automated genome-wide screen was performed on fifteen individuals in kindred 4415 (FIG. 2A) using the ABI marker index of 400 polymorphic markers. Markers were distributed across the genome at ~10-20 cM intervals. The fluorescently labeled markets were used to amplify genomic DNA in total reaction volumes of 20 µl in an MJRPTC-200 thermocycler (MJ Research). The products were visualized on an Applied Biosystems Model 373A and analyzed by the Genotyper peak-calling software. Pairwise linkage analysis was performed using the MLINK program of the LINKAGE package. Lathrop, G. M. et al. (1985) *Am J Hum Genet* 37,482-98. Disease penetrance was set at 0.95 without a gender difference, and the normal and disease allele frequencies were set at 0.999 and 0.001, respectively.

KCNJ2, CACNG1 and SCN4A Are Candidate Genes for Andersen's Syndrome

The region of chromosome 17q23 defined by the obligate recombinant boundaries of proximal marker D17S787 and distal marker 17S784 was examined in the mapviewer database Candidate genes were selected based on their location within these boundaries as ascertained from the available physical map. The entire coding region of Kir2.1 was amplified (about 1.6 kb) from genonile DNA in all individuals from kindred 4415. PCR primer sequence is as follows: F1 5' CCAAAGCAGAAGCACTGGAG 3' (SEQ ID NO.: 3) and R1 5' AATCAAATACCCAACCAAGGC 3' (SEQ ID NO.: 4). 50 µl PCR reactions were performed on 100 ng of genomic DNA and 20 pmol of each F1 and R1 PCR primers using Clonetech's Advantage-GC cDNA polymerase and buffers. The GC-meltmix was used at a final concentration 1.0 mM, and reactions were cycled under the following protocol: 94° C.–2 min, (94° C.–10 sec, 60° C.–20 sec, 68° C.–2 min)×45, 68° C.–2 rain and 30 sec, 4 C.–hold. These products were prepared using the Qiaquick PCR spin prep kit (Qiagen) and were sequenced using the following primers: F1, R1, F2 5' GTGTTTGATGTGGC-GAGTGG 3' (SEQ ID NO.: 5) and R2 5' ATTCCACTGT-CAAACCCAAC 3' (SEQ ID NO.: 6). Sequencing was performed by the Core facility at the University of Utah. Substitution mutations were checked in over 100 unaffected unrelated individuals either by SSCP analysis or by mutation-specific PCR analysis (See Table 1). For these individuals, genonfic DNA was PCR amplified using the above protocol. These reactions were ten diluted in 100 µl of water and served as templates with which to perform SSCP analysis or mutation-specific PCR (MSP) analysis. For SSCP and MSP, 2 µl of diluted PCR reaction was used as template DNA. SSCP was performed with 10 µl reactions as described previously. Ptacek, L. J. et al. (1991) *Cell* 67, 1021-7. Products were electrophoresed according to Table 1 and visualized using standard techniques. MSP analysis was performed on four mutations that could not be visualized using SSCP. Individuals were PCR amplified using either the forward (F) and reverse (R) control primers or the forward mutant (M) primer and the reverse control primer. Products were electrophoresed side-by-side on a 1% agarose gel.

Previous findings that periodic paralysis and LQT are associated with mutations in ion channels led to the prediction that AS might also be due to this same mechanism. Chromosome 17q23 contigs contained three ion channel genes within the linked region, KCNJ2, calcium channel CACNG1, and sodium channel SCN4A (FIG. 3). These channels are expressed in skelet al muscle and heart. Two findings led to focusing on KCNJ2: 1) a non-obligatere combination between the most highly linked marker and CACNG1 and SCN4A in kindred 4415 (data not shown) was identified, and 2) SCN4A had already been shown to be responsible for periodic paralysis without heart or developmental problems. Ptacek, L. J. et al. (1991) *Cell* 67:1021-7. Due to the known function and expression pattern of Kir2.1, KCNJ2 is an excellent candidate gene for Andersen's Syndrome.

D71V Segregates with Andersen's Syndrome

The coding region of KCNJ2, contained within one exon, was PCR amplified and sequenced in all individuals from kindred 4415 from whom DNA was available. This excludes the deceased individual in the first generation. An A to T transversion corresponding to the mutation D71V was identified in all affected individuals but not in any unaffected family members (FIG. 1A and 1B). DNA from over 100 unaffected unrelated individuals was examined for this base pair change using mutation-specific PCR, and the change was never observed. This residue is absolutely conserved not only between human and rodent, but also in all identified families of the inward rectifier $K^+$ subunits (FIG. 1C). This mutation lies in the cytoplasmic N-terminal segment of Kir2.1 (FIG. 1B) in a region of unknown function.

Additional Mutations Have Been Identified in Andersen's Syndrome Probands

Figure 4:
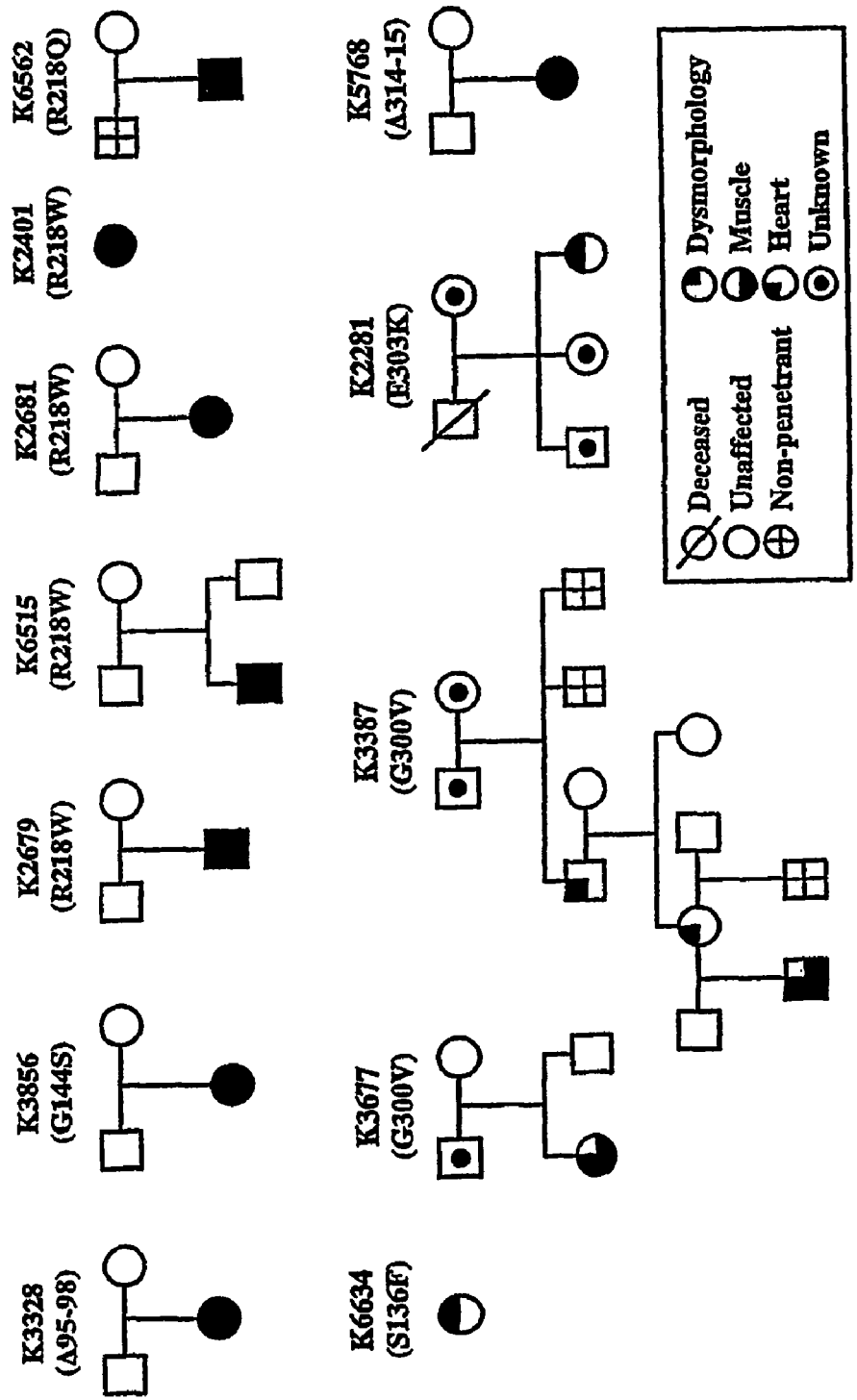
FIG. 4 shows the pedigree of additional AS kindreds with identified mutations in Kir2.1. Females are denoted with circles and males with squares. The kindred number and mutation are denoted above each pedigree. Families in which the first generation is marked as "unaffected"0 represent de novo mutations. "Uncertain" individuals are those for whom there was no clinical data.
Figure 5:
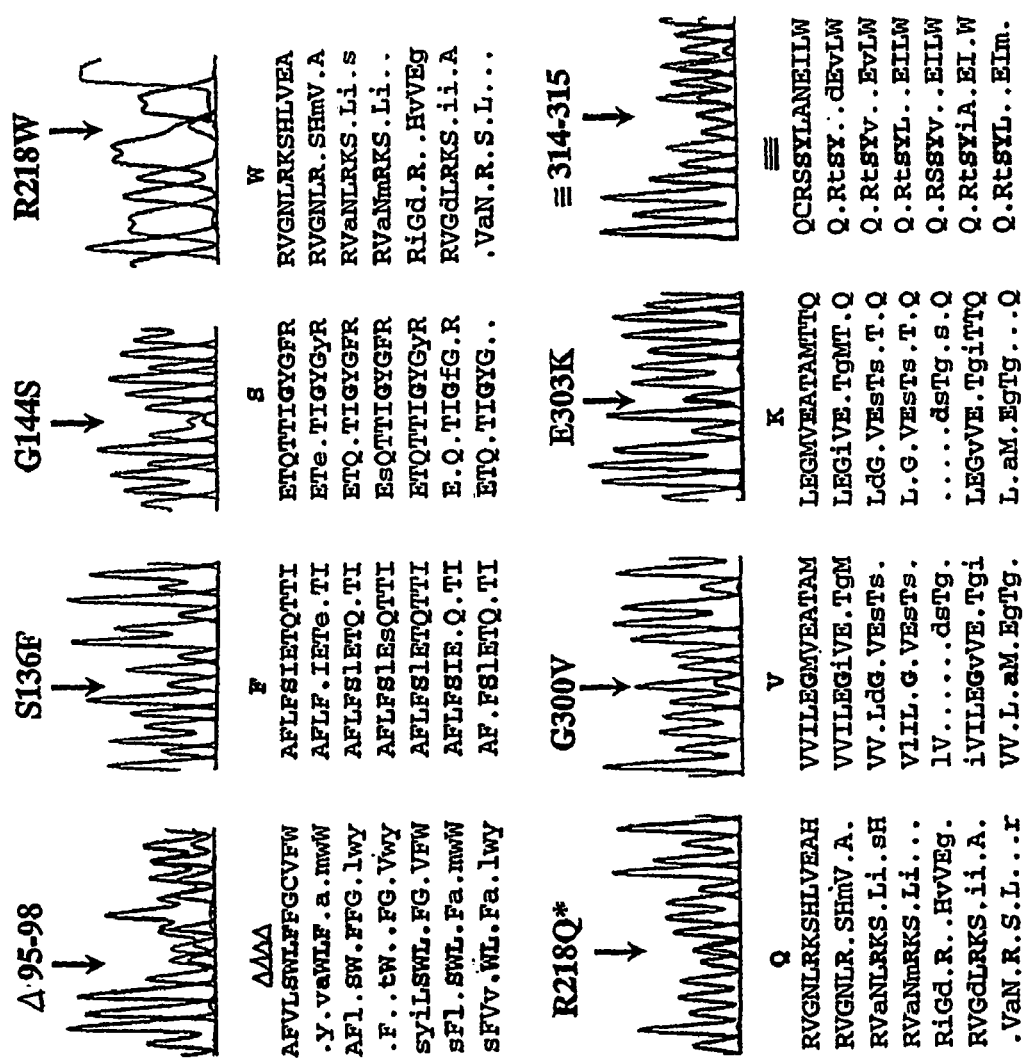
FIG. 5 is a series of graphs illustrating sequence chromatography of affected AS individuals. Mutations of Kir2.1 in Andersen's patients occur in highly conserved residues. Chromatographs of the nucleotide sequence corresponding to each mutation are shown. "*" indicates that the nucleotide sequence shown is the reverse complement of coding sequence. Below each chromatograph is an alignment of the first member of all human Kir families. Mutant residues are denoted above each alignment. "Δ" marks a deletion of the residue below it. Lowercase letters denote conservative amino acid changes, whereas a "." denotes a non-conservative amino acid change.

Subsequently thirty-one additional unrelated AS probands (FIG. 4) for mutations in KCNJ2 were examined. As with kindred 4415, the coding region of KCNJ2 was PCR amplified and sequenced. In total, fourteen mutations were identified in twenty-two probands (FIGS. 4 and 5). Three of the sixteen families examined do not have any mutations in the coding region of KCNJ2. No discernible difference was observed in the clinical manifestations between kindreds with Kir2.1 mutations and those without a definable mutation. The mutations occur at highly conserved residues (FIG. 5) and include: D71V, Δ95-98, S136F, G144S, R218W, R218Q, G300V, E303K, and Δ314-15. Twelve of the fourteen mutations are missense mutations consisting of the following changes (Genbank accession #AF153819): D71V (A440T), S136F (T635C), G144S (G658A), R218W (C880T),R218Q (G881A), G300V(G1127T), E303K (G1135A), N216H (A874C), V302M (G1132A), P186L (C785T), C52G (T75R), and D71N (G439A). Two mutations are in-frame deletions: Δ95-98 (bp 513-524) and Δ314-15 (bp 1167-1172). All substitution mutations were checked in over 100 unaffected unrelated individuals by SSCP or mutation-specific PCR analysis (Table 1) and were never seen in this panel. R218W occurred in five families, and G300V is present in two families. All other mutations were only identified in single families. At least three of the changes represent de novo mutations (G144S, R218W (three events), and Δ314-15). Only one polymorphism was identified in AS probands. This polymorphism is a silent mutation of C1374T in the codon for residue L382.

from being inserted into the membrane. S136F and G144S are both pore mutations. G144S is located in the first position of the highly conserved K$^+$ channel signature sequence GYG. Several mutations reside in the C-terminus. R218W and R218Q are located within the C-terminal interaction domain, and G300V, E303K, and Δ314-15 are located in a region without a described function. Tinker, A. et al. (1996) *Cell* 87: 857-68.

D71V and R218W Result in a Dominant Negative Effect on Kir2.1 Current in *Xenopus* Oocytes The ability of mutant Kir2.1 subunits to form functional homomultimeric channels was assessed by comparing oocytes injected with wild-type (WT) or mutant Kir2.1 CRNA (23 ng/oocyte). Injection of WT Kir2.1 induced nearly instantaneous K$^+$ currents that demonstrated strong inward rectification (FIGS. 6A and 7A), as previously described. Raab-Grahan, K. F. et al. (1994) *Neuroreport* 5,2501-5. Inward rectification refers to the property that permits inward flux of K$^+$ ions at potentials negative to the K$^+$ equilibrium potential ($E_K$) more readily than outward flux at positive potentials. At extreme hyper polarized potentials, the currents decayed due to voltage and time-dependent blockade by external Na$^+$ ions. Biermans, G. et al. (1987) *Pflugers Arch* 410:604-13. D71V and R218W mutant

TABLE 1

Primer sequences and mutational analysis conditions. "T$_a$" refers to the PCR annealing temperature. Visualization of PCR products was by 1% agarose gel electrophoresis except where denoted by an "*" next to the mutation. These exceptions were visualized using standard SSCP techniques. See "Mutational analysis" in the experimental methods section.

| Mutation | Primer sequence | | | Method | T$_a$ |
|---|---|---|---|---|---|
| D71V | F 5' GGCAACGGTACCTCGCAGA 3' | SEQ ID. NO.: 7 | | MSP | 62° C. |
| | M 5' GGGAACGATACCTCGCAGT 3' | SEQ ID. NO.: 8 | | | |
| | R 5' CAACCAAAACACACAGCCAAA 3' | SEQ ID. NO.: 9 | | | |
| S136F | F 5' CGGCTGCCTTCCTCTTCTC 3' | SEQ ID. NO.: 10 | | MSP | 64° C. |
| | M 5' CGGGTGCCTTCCTCCTCTT 3' | SEQ ID. NO.: 11 | | | |
| | R 5' GTTTCTCTTCTTTGGCTTTGC 3' | SEQ ID. NO.: 12 | | | |
| G144S* | F 5' GCTTCACGGCTGCCTTCC 3' | SEQ ID. NO.: 13 | | SSCP | 55° C. |
| | R 5' GTTTCTCTTCTTTGGCTTTGC 3' | SEQ ID. NO.: 14 | | | |
| R218Q | F 5' GGCGAGTGGGCAATCTTCG 3' | SEQ ID. NO.: 15 | | MSP | 62° C. |
| | M 5' GGCGAGTAGGCAGTCTTCA 3' | SEQ ID. NO.: 16 | | | |
| | R 5' CTCAAATCATATAAAGGACTGTC 3' | SEQ ID. NO.: 17 | | | |
| R218W | F 5' GGCGAGTGGGCAATCTTCG 3' | SEQ ID. NO.: 18 | | MSP | 57° C. |
| | M 5' GTCGCGAGTAGGCAATGTTT 3' | SEQ ID. NO.: 19 | | | |
| | R 5' CTCAAATCATATAAAGGACTGTC 3' | SEQ ID. NO.: 20 | | | |
| G300V* | F 5' AGGACATTGACAACGCAGAC 3' | SEQ ID. NO.: 21 | | SSCP | 55° C. |
| | R 5' CATGGCAGTGGCTTCCACC 3' | SEQ ID. NO.: 22 | | | |
| E303K | F 5' CATACTGGAAGGCATGGTGG 3' | SEQ ID. NO.: 23 | | MSP | 63° C. |
| | M 5' CATGCTGGAAGGAATGGTGA 3' | SEQ ID. NO.: 24 | | | |
| | R 5' GTTTTGTGGAACCTGGAATAG 3' | SEQ ID. NO.: 25 | | | |

Figure 2:
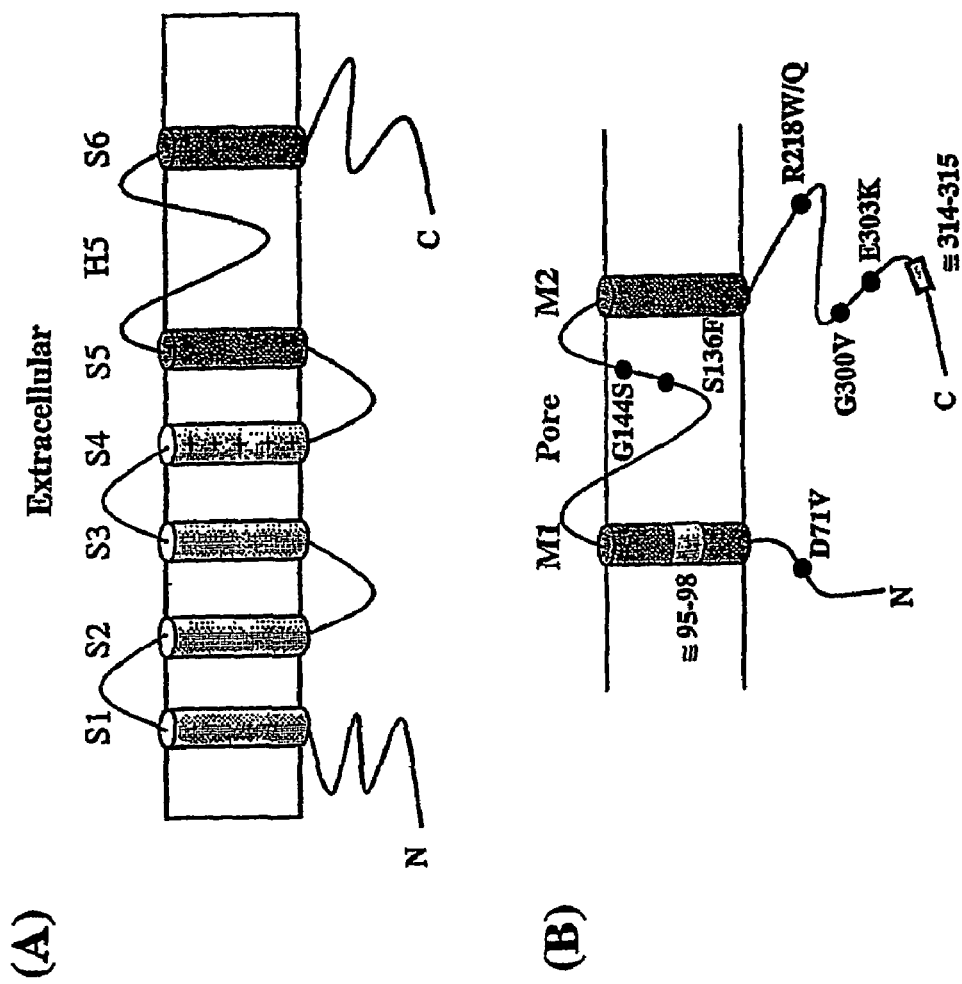
FIGS. 2A and 2B depict the structure of Kir2.1 in relationship to voltage-gated $K^+$ channels.
Figure 6:
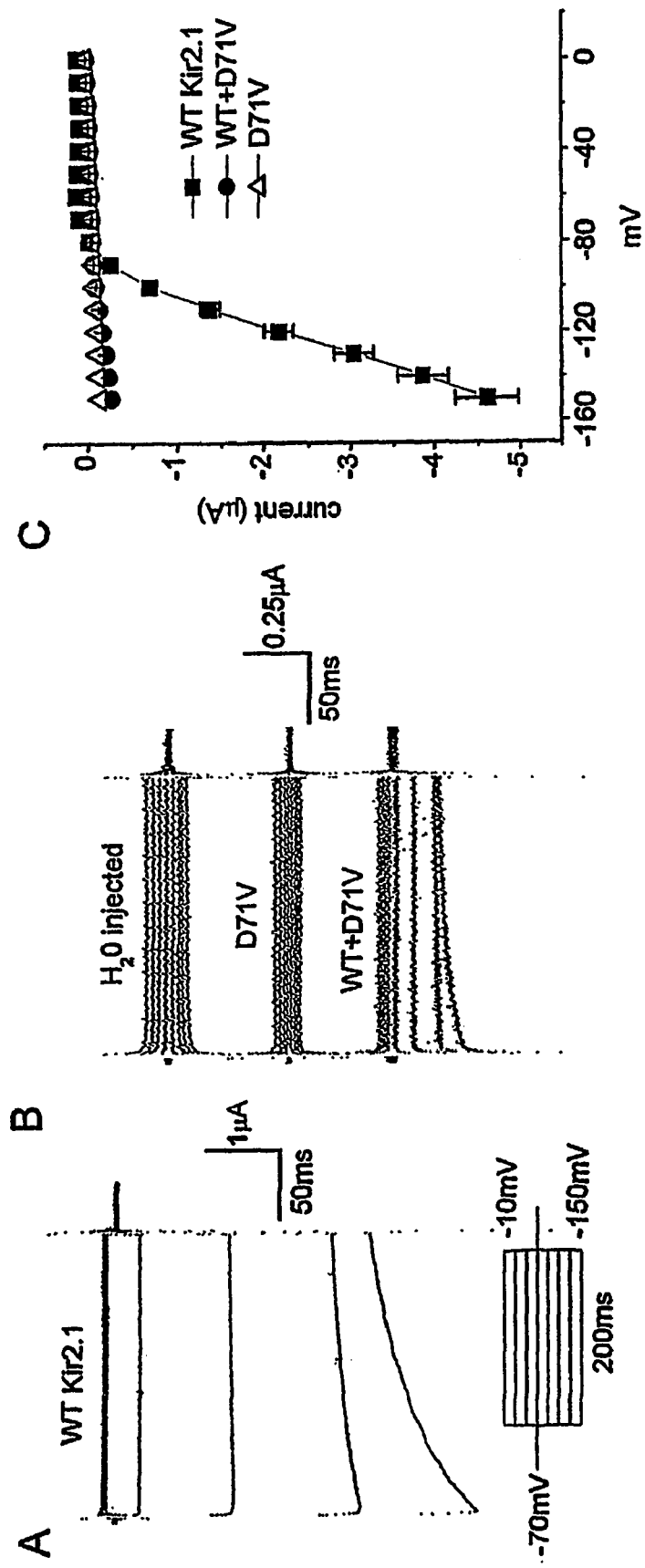
FIGS. 6A through 6C depict the functional effects of D71V Kir2.1 mutation.
Figure 7:
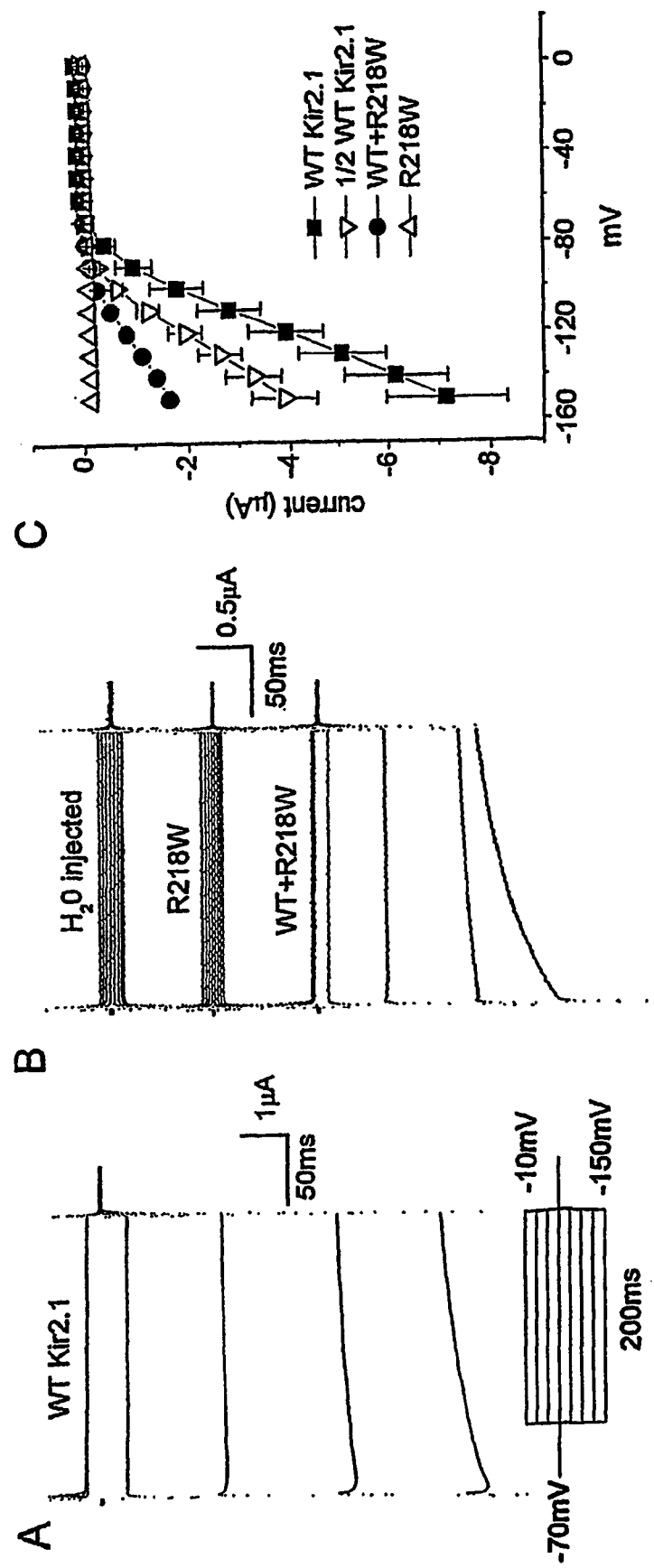
FIGS. 7A through 7C depicts the functional effects of R218W Kir2.1 mutation.

The mutations are located throughout the protein (FIG. 2B). D71V resides in the N-terminus in the last position of a predicted alpha-helix. This residue is just C-terminal to the putative N-terminal interaction domain. Tucker, S. J., & Ashcroft, F. M. (1999) *J Biol Chem* 274: 33393-7. Deletion Δ95-98 removes four residues of the M1 transmembrane segment. This might completely prohibit the M1 segment subunits failed to form functional homomultimeric channels. Injection of D71V or R218W cRNA did not induce detectable K$^+$ currents (FIGS. 6B and 7B). Small endogenous currents, identical to those in H$_2$O-injected control oocytes, were recorded in oocytes injected with mutant cRNA.

AS is an autosomal-dominant disorder and, as such, affected individuals possess one normal and one mutant KCNJ2 allele. To assess the ability of mutant Kir2.1 subunits to form functional heteromultimeric channels with WT subunits, mutant (11.5 ng/oocyte) and WT Kir2.1 cRNA (11.5 ng/oocyte) were co-injected and compared currents to those induced by injection of WT Kir2.1 cRNA (23 ng/oocyte). Co-expression of WT and D71 V Kir2.1 induced an inwardly rectifying K$^{30}$ current whose current amplitude was markedly reduced (FIG. 6B and 6C). Current amplitude at −150 mV was −4.61±0.37 µA for WT Kir2.1, compared to −0.26±0.02 µA for co-injected WT and D71V. Assuming random association of WT and mutant Kir2.1 subunits, 1/16 of the channels will be comprised of four WT subunits, whereas 15/16 of channels will contain one or more mutant subunits. The reduction in current induced by co-expression of WT and D71V subunits was approximately 15/16 that of WT current, suggesting that one mutant D71V subunit is sufficient to eliminate channel function. Co-expression of WT and R18W Kir2.1 also induced inwardly rectifying K$^+$ currents, although the magnitude of current reduction was not as severe as that seen with D71V subunits (FIGS. 7B and 7C). These findings demonstrate that D71V and R218W subunits co-assemble with WT Kir2.1 subunits and cause variable degrees of dominant-negative suppression of channel function.

SUMMARY

In summary, mutations in the Kir2.1 gene, KCNJ2, are responsible for Andersen's Syndrome. Humans affected with Andersen's Syndrome have a high risk for fatal cardiac dysrhythmias. The phenotypic expression of Andersen's Syndrome varies widely with some affected individuals potentially going undiagnosed. Thus, a method of diagnosing Andersen's Syndrome is presented. The method uses a genome screen for mutations in KCNJ2. Moreover, similar screens are provided which may determine if an individual seemingly unaffected by Andersen's Syndrome or other long QT disorders may in fact have a heightened risk for a potentially fatal cardiac dysrhythmia.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

---

The invention claimed is:

1. A method of diagnosing Andersen's Syndrome in a human subject comprising:
   a) screening for an alteration in a copy of the KCNJ2 gene of the human subject, wherein the KCNJ2 gene comprises SEQ ID NO: 1 as altered by one or more alterations, wherein said one or more alterations are selected from A440T, T635C, G658A, C880T, G881A, G1127T, or G1135A; and
   b) detecting said alteration in a copy of the KCNJ2 gene of the human subject, wherein detection of said alteration diagnoses Andersen's Syndrome in said subject.

2. The method of claim 1, wherein the screening for an alteration in a copy of the KCNJ2 gene comprises comparing the sequence of the copy of the KCNJ2 gene from the subject with a sequence of a wild-type KCNJ2 gene.

3. The method of claim 1, wherein the screening for an alteration in a copy of the KCNJ2 gene comprises analyzing the sequence of the copy of the KCNJ2 gene by SSCP analysis or mutation-specific PCR analysis.

4. The method of claim 1, wherein the screening for an alteration in a copy of the KCNJ2 gene comprises sequencing a copy of the KCNJ2 gene from the human subject and comparing the sequence of the copy of the KCNJ2 gene to a sequence with an alteration in the KCNJ2 gene, wherein the sequence of the KCNJ2 gene that is identical to the sequence with an alteration in the KCNJ2 gene indicates an alteration in the copy of the KCNJ2 gene from the human subject.

5. The method of claim 1, further comprising obtaining a tissue sample from the human subject, isolating a copy of the KCNJ2 gene of the human subject, sequencing the isolated copy of the KCNJ2 gene, and comparing the sequence of the copy of the KCNJ2 gene from the subject with a sequence of a wild-type KCNJ2 gene.

* * * * *